United States Patent
Hashimoto

(10) Patent No.: US 7,629,599 B2
(45) Date of Patent: Dec. 8, 2009

(54) MULTI-LEAF COLLIMATOR AND A RADIOTHERAPY UNIT PROVIDED WITH THE SAME

(75) Inventor: Teruo Hashimoto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 310 days.

(21) Appl. No.: 11/669,980

(22) Filed: Feb. 1, 2007

(65) Prior Publication Data

US 2007/0176126 A1 Aug. 2, 2007

(30) Foreign Application Priority Data

Feb. 2, 2006 (JP) .............................. 2006-025383

(51) Int. Cl.
G21K 1/04 (2006.01)
(52) U.S. Cl. .................................. 250/505.1; 378/152
(58) Field of Classification Search ............. 250/505.1, 250/492.1; 378/65, 147, 152, 153
See application file for complete search history.

(56) References Cited

U.S. PATENT DOCUMENTS

| | | | |
|---|---|---|---|
| 5,394,452 A * | 2/1995 | Swerdloff et al. | ............. 378/65 |
| 6,618,467 B1 * | 9/2003 | Ruchala et al. | ............... 378/65 |
| 6,931,100 B2 * | 8/2005 | Kato et al. | ................... 378/152 |
| 7,132,674 B2 * | 11/2006 | Pastyr et al. | ............. 250/505.1 |
| 2004/0022363 A1 | 2/2004 | Ghelmansarai | |
| 2005/0013406 A1 | 1/2005 | Dyk et al. | |

FOREIGN PATENT DOCUMENTS

| | | |
|---|---|---|
| EP | 0 193 509 A2 | 9/1986 |
| EP | 0 314 231 A2 | 5/1989 |

OTHER PUBLICATIONS

U.S. Appl. No. 12/035,143, filed Feb. 21, 2008, Hashimoto.
K. Luchka, et al., "Assessing radiation and light field congruence with a video based electronic portal imaging device", Med. Phys., vol. 23, No. 7, XP-002430881, Jul. 1996, pp. 1245-1252.

* cited by examiner

*Primary Examiner*—Kiet T Nguyen
(74) *Attorney, Agent, or Firm*—Oblon, Spivak, McClelland, Maier & Neustadt, L.L.P.

(57) ABSTRACT

A multi-leaf collimator that narrows a radiation field to a predetermined shape is provided with leaf blocks movable in the direction of the radiation field and having pattern images drawn along the direction of movement on a predetermined surface, and detection part acquiring an image of fixed-point via fixed-point observation in the direction of that predetermined surface and for detecting displacement of said leaf blocks based on the arranged locations of the pattern images existing in this image of fixed-point. Moreover, it is provided with detection part acquiring an image of fixed-point via fixed-point observation in the direction of that predetermined surface and for detecting the locations of the leaf blocks based on the arranged locations of the pattern images existing in this image of fixed-point. According to the present invention, displacement and locations of leaf blocks can be detected without making contact, and displacement due to the effect of backlash and gear wear or errors in detecting locations can be prevented. Therefore, regardless of backlash, the locations of the leaf blocks can be detected with high precision, and the radiation field can be matched to the shape of an affected part with high precision.

28 Claims, 18 Drawing Sheets

MULTI-LEAF COLLIMATOR AND A RADIOTHERAPY UNIT PROVIDED WITH THE SAME

BACKGROUND OF THE INVENTION

1. Field of the Invention

The present invention relates to a multi-leaf collimator that narrows the radiation field emitted to an object and a radiotherapy unit provided with the same.

2. Description of the Related Art

Radiation therapy has been widely used as treatment for affected parts such as cancer and tumors. This radiation therapy is treatment with the destruction of tissue cells in an affected part, inhibition of cell division, or the like by emitting radiation to the affected part. It is important to precisely irradiate an affected part in such radiation therapy. By precisely irradiating an affected part, damage to normal cells around an affected part can be minimized, thereby enabling effective irradiation to an affected part.

In order to ensure precise irradiation, generated radiation is narrowed with a diaphragm part or multi-leaf collimator so that the shape of the radiation field becomes similar to that of the affected part. A multi-leaf collimator comprises a plurality of leaf blocks and a movable mechanism paired with these leaf blocks. The leaf blocks are made of a material such as tungsten that absorbs radiation. By moving the leaf blocks between a radiation source and sites where there is no need to emit radiation, a radiation field is narrowed to a predetermined shape (e.g., refer to Japanese Published Unexamined Application No. 1999-216197).

This movable mechanism is shown in FIG. 1. As shown in FIG. 1, the movable mechanism is provided with a drive motor M, which is a motor with a reducer, and an output gear OG. The leaf blocks are moved with the drive power transmitted from the output gear OG. A plurality of transmission gears TG are arranged between the drive motor M and output gear OG, respectively rotating as they engage with each other, thereby transmitting drive power from the drive motor M to the output gear OG.

In this movable mechanism, location detection part such as an encoder E or potentiometer P are placed on one of the multiple transmission gears TG. Displacement of the leaf blocks is correlated with the amount of rotation of the drive motor M, output gear OG, and the plurality of transmission gears TG. The encoder E and potentiometer P detect the locations of the leaf blocks by detecting the rotation of the transmission gears TG. Furthermore, although the encoder E and potentiometer P have the same function, they both may be arranged for redundancy.

Thus, if a movable mechanism comprises a plurality of gears as above, backlash occurs at each of the gears. With the method of detecting the locations of the leaf blocks based on rotation of one of the multiple gears, errors due to backlash are observed between the detected locations of the leaf blocks and the actual locations thereof.

It is possible to minimize errors caused by backlash, such as by correcting the detected locations of the leaf blocks with the backlash of each gear. However, gears engage with each other physically, so the tops of the teeth become worn over time. As this wear progresses over time, errors caused by backlash will increase. Therefore, even if the locations are corrected with pre-calculated backlash, errors will gradually increase, resulting in decreased accuracy of specifying the locations of the leaf blocks over time.

It is preferable to keep errors in shape between an affected part and a radiation field to within 1 mm around the location of the affected part. Thus, the difference in locations of the leaf blocks must be kept to approximately 0.3 mm. This is based on the ratio of distance between the surface of an installed multi-leaf collimator from a radiation source and the location of an affected part therefrom. Therefore, errors in detected locations caused by backlash affect therapeutic effectiveness to a considerable degree.

SUMMARY OF THE INVENTION

This invention is intended to provide a multi-leaf collimator that avoids the effect of backlash in detecting the displacement or locations of leaf blocks and that precisely detects the displacement or locations of leaf blocks and to provide the radiotherapy unit provided with the same.

In the first aspect of this invention, a multi-leaf collimator that narrows a radiation field to a predetermined shape is provided with leaf blocks movable in the direction of the radiation field and a detecting element that detects the displacement or locations of the leaf blocks. The leaf blocks are provided with pattern images drawn along the direction of movement on a predetermined surface. Moreover, the detecting element acquires an image of fixed-point via fixed-point observation in the direction of said predetermined surface and detects the displacement or locations of said leaf blocks based on the arranged locations of the pattern images existing in this image of fixed-point.

In the second aspect of this invention, a radiotherapy unit is provided with a radiation source for irradiating radiation, a bed on which to place the object, and a multi-leaf collimator between the radiation source and the bed that narrows a radiation field irradiated from said radiation source to a predetermined shape. The multi-leaf collimator is provided with leaf blocks movable in the direction of the radiation field and a detecting element that detects the displacement or locations of the leaf blocks. The leaf blocks are provided with pattern images drawn along the direction of movement on a predetermined surface. Furthermore, the detecting element acquires an image of fixed-point via fixed-point observation in the direction of said predetermined surface and detects the displacement or locations of the leaf blocks based on the arranged locations of the pattern images existing in this image of fixed-point.

According to the first and second aspects 1 and 2 of this invention, the displacement and locations of the leaf blocks can be detected without making contact, and errors due to the effect of backlash and gear wear in detecting the displacement and the locations can be prevented. Therefore, regardless of backlash, the locations of leaf blocks can be detected with high precision, and the radiation field can be matched to the shape of the affected part with high precision.

DETAILED DESCRIPTION OF THE EMBODIMENT

Embodiment 1

Figure 1:
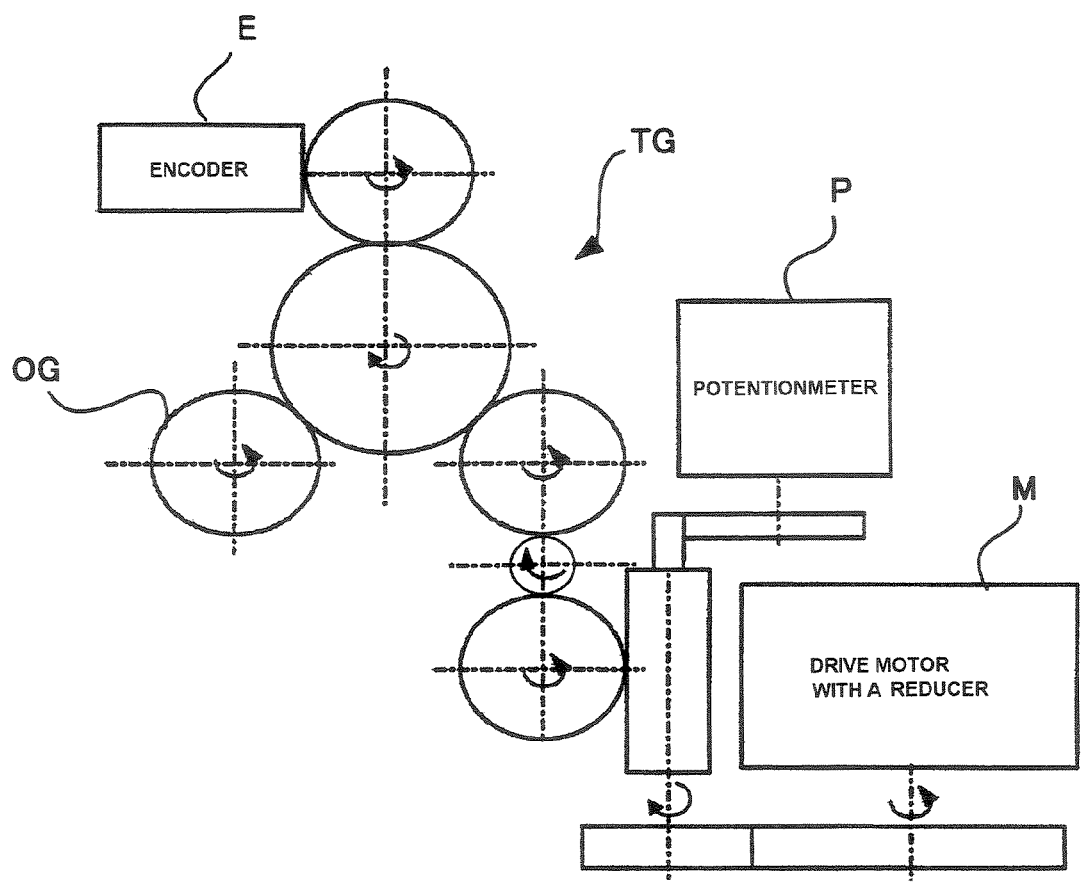
FIG. 1 shows a conventional movable mechanism that displaces leaf blocks.
Figure 2:
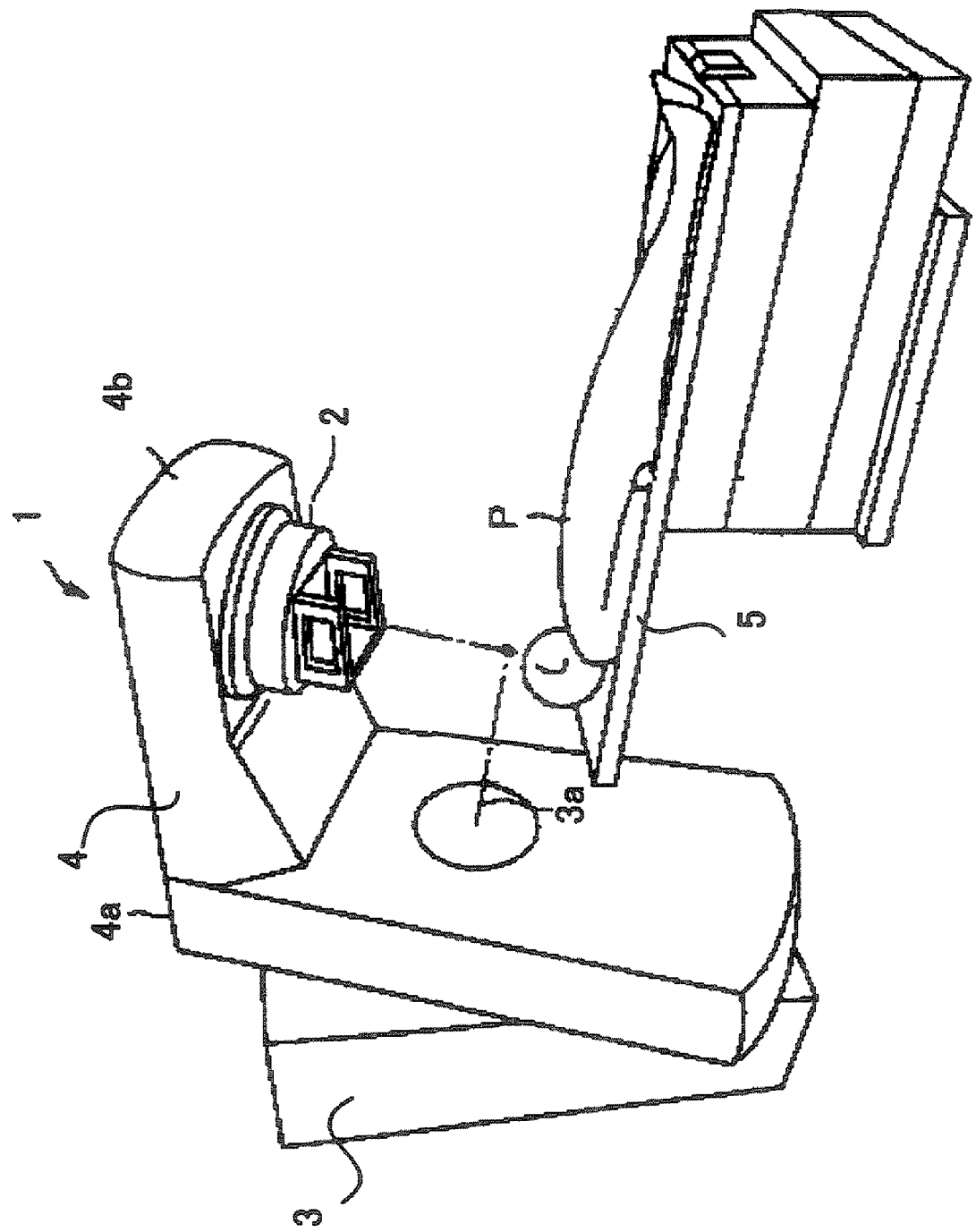
FIG. 2 is an external view showing the example of one configuration of a radiotherapy unit related to Embodiments 1 to 5.

FIG. 2 is an external view showing a radiotherapy unit 1 related to this embodiment. The radiotherapy unit 1 is an apparatus for treating the affected part of an object P. The radiotherapy unit 1 treats the affected part by emitting radiation at the affected part of the object P.

This radiotherapy unit 1 is provided with a radiation head 2 that generates radiation and a bed 5 on which the object P is placed. The radiation head 2 and bed 5 are arranged facing each other. Radiation generated in the radiation head 2 is emitted in the direction toward the bed 5.

This radiotherapy unit 1 is fixed with a fixing gantry 3 on the surface on which the apparatus is installed. A rotating gantry 4 is supported by this fixing gantry 3 in the air. The radiation head 2 is installed on this rotating gantry 4. The rotating gantry 4 is a rough L-shaped steric figure. The rotating gantry 4 has an arm 4a supported by the fixing gantry 3, and the radiation head 2 is installed on the other arm 4b. The radiation head 2 is facing the direction of the bed S.

In radiation therapy, it is necessary to precisely match the affected part of the object P placed on the bed 5 and the isocenter of radiation. Therefore, the rotating gantry 4 is supported by the fixing gantry 3 through a turning shaft 3a. By turning the rotating gantry 4 around the turning shaft 3a, the direction of the radiation head 2 will change. By changing the direction of the radiation head 2, the radiation to be generated is emitted at different angles, so the isocenter can be changed around the turning shaft 3a.

Furthermore, the bed 5 is movable in the direction of the body axis of the object P, the direction of the radial axis of radiation, and the direction of rotation to remain parallel with the installation surface of the radiotherapy unit 1. Movement in these directions allows the location of the isocenter to change, matching the isocenter with the affected part in combination with the rotation of the rotating gantry 4.

Figure 3:
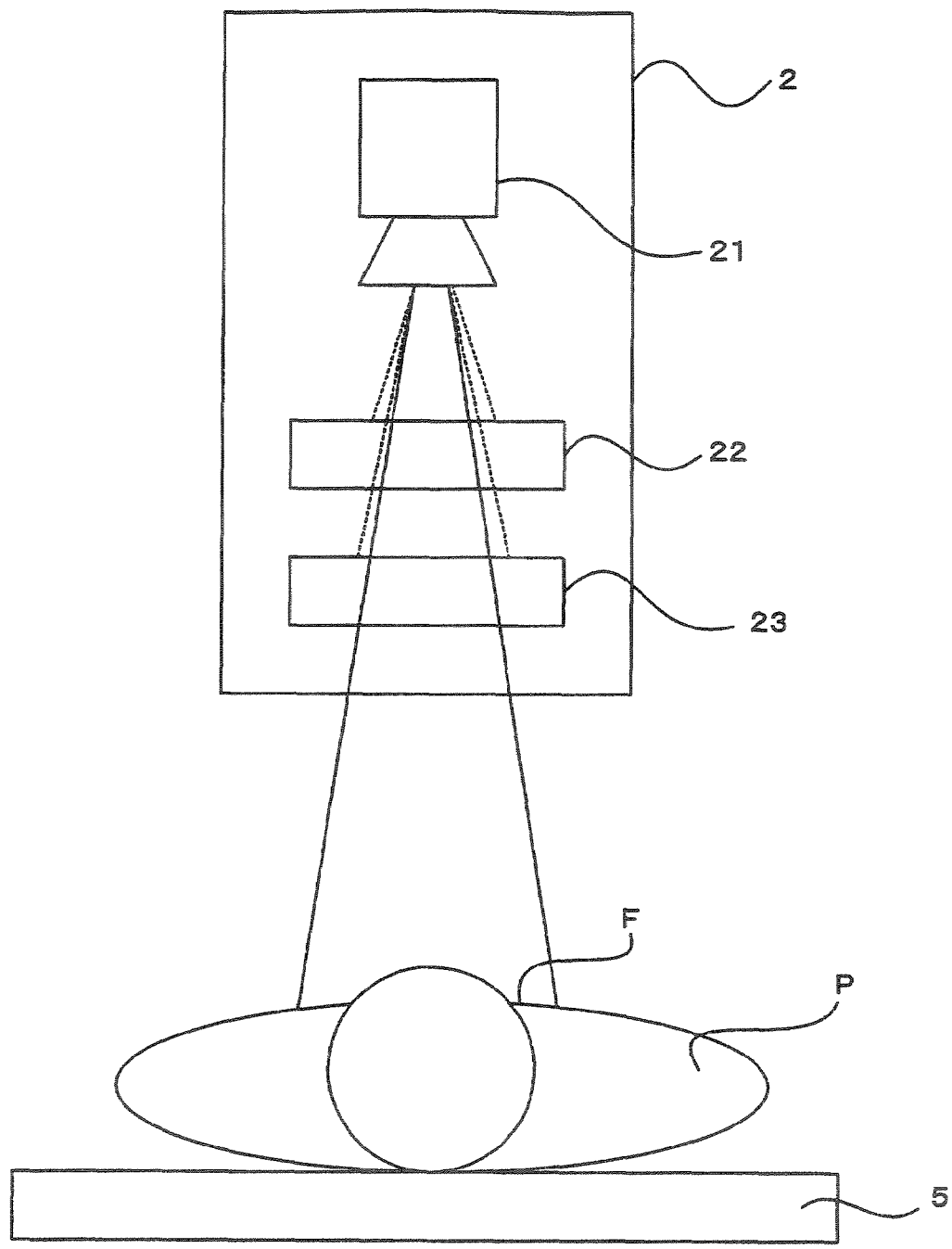
FIG. 3 shows the basic structure of a radiotherapy unit related to Embodiments 1 to 5.

FIG. 3 is a view showing the basic structure of the radiotherapy unit 1. As shown in FIG. 3, a radiation source 21, a diaphragm part 22 and a multi-leaf collimator 23 are placed within the radiation head (head) 2 collaterally in the direction toward the bed 5.

The radiation source 21 comprises an electron accelerator, the target of the electron beam, and so on. Radiation is generated by accelerating electrons with the electron accelerator and colliding them against the target of the electron beam (target). Radiation that is generated may be a photon beam (X-ray and γ-ray, etc.), electron beam, heavy particle beam (proton, helium, carbon, neon, π meson beam, neutron ray, and so on), and so forth.

The diaphragm part 22 and the multi-leaf collimator 23 are arranged in the range of radiation, narrowing the range of radiation and creating a radiation field F that matches the shape of the affected part. The diaphragm part 22 comprises a block pair facing each other over the radiation axis. The material of the block pair possesses a property of absorbing radiation such as tungsten. This block pair narrows the range of radiation by bringing them together or separating them.

Figure 4:
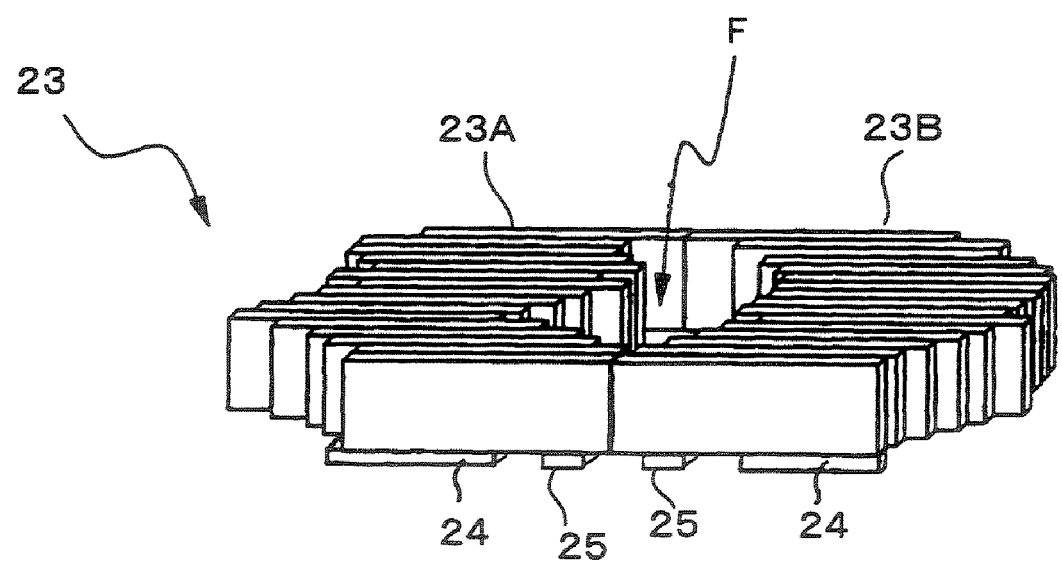
FIG. 4 is a perspective view showing the multi-leaf collimator provided with a radiotherapy unit related to Embodiments 1 to 5.

FIG. 4 is a perspective view showing the multi-leaf collimator 23. The multi-leaf collimator 23 comprises leaf blocks 23A and 23B facing each other over the radiation axis. The leaf blocks 23A and 23B have tapered cross-sectional surfaces and arch-like side surfaces with short perimeters. Moreover, the material possesses a property of absorbing radiation such as tungsten. A plurality of pairs of leaf blocks 23A and 23B are placed close to or in contact with each other in the direction of the side surfaces.

A movable mechanism 24 is placed on each of the leaf blocks 23A and each of the leaf blocks 23B. The movable mechanism 24 displaces each of the leaf blocks 23A or 23B targeted for movement with the same circular orbit, with the radiation source 21 as the center of the direction of movement. With this movable mechanism 24, pairs of leaf blocks 23A and 23B are moved toward or separate from each other, narrowing the radiation field F to the appropriate shape. Radiation emitted to places other than the radiation field F is absorbed by the leaf blocks 23A and 23B, and only radiation that passes through the radiation field F will pass through the multi-leaf collimator 23.

Furthermore, a detecting element 25 is placed on each of the leaf blocks 23A and each of the leaf blocks 23B. The detecting element 25 detects displacement of the leaf blocks 23A or 23B respectively targeted for detection. Displacement indicates the vector for showing changes in locations, including direction of movement and distance.

The result of displacement detection with the detecting element 25 is fed back to the movable mechanism 24. The multi-leaf collimator 23 displaces each of the leaf blocks 23A and 23B to the intended location according to the feedback of the result of displacement detection, and creates a radiation field F that matches the shape of the affected part. Differences between the accumulated results of displacement detection and intended locations are calculated, and each of the leaf blocks 23A and 23B is displaced so as to eliminate the differences.

Figure 5:
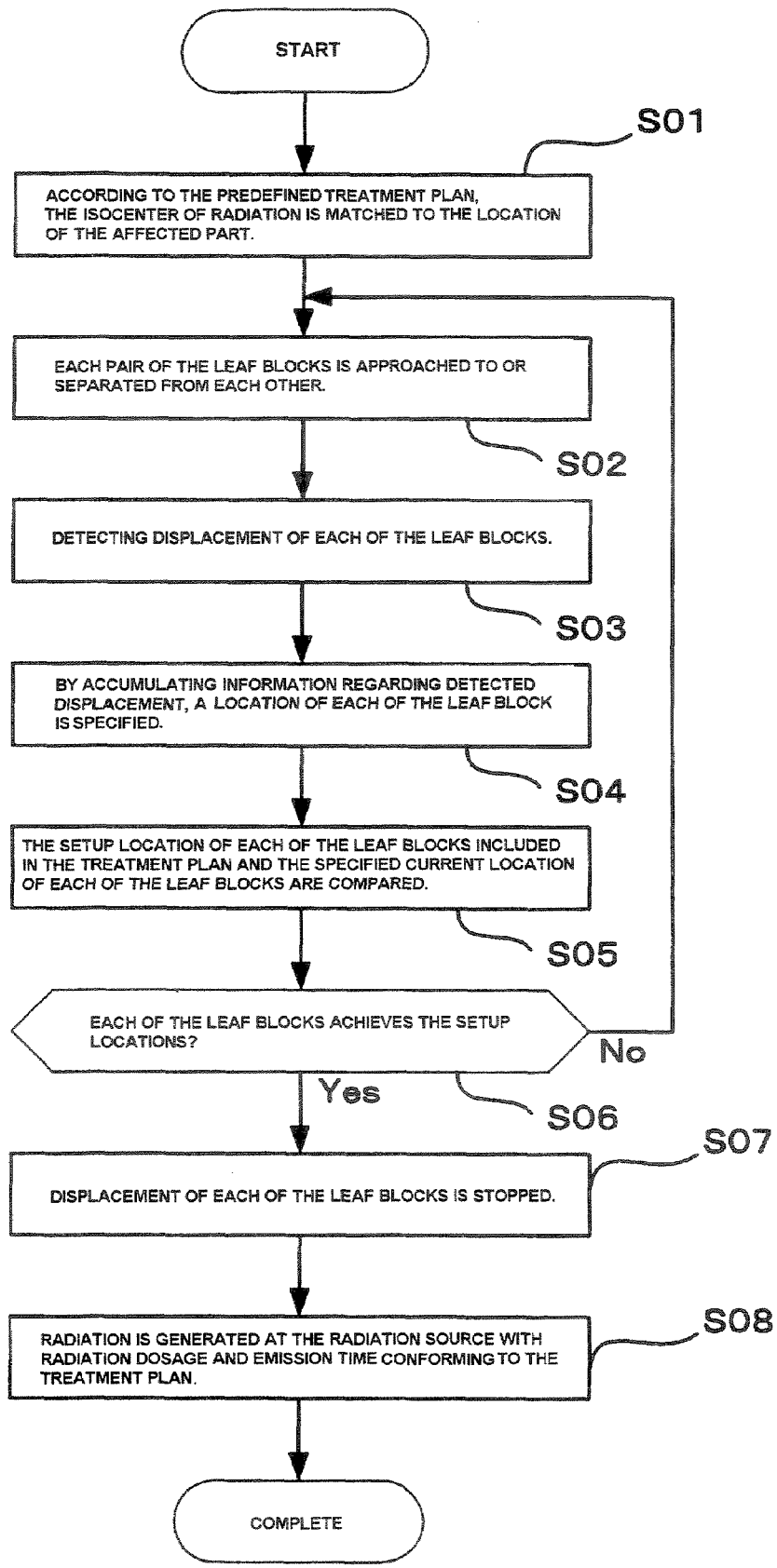
FIG. 5 is a flowchart showing the brief operation of a radiotherapy unit related to Embodiments 1 to 5.

A simplified operation of the radiotherapy unit 1 will be described below based on FIG. 5. FIG. 5 is a flowchart showing the simplified operation of the radiotherapy unit 1.

First, with the radiotherapy unit 1, according to the predefined treatment plan, the rotating gantry 4 is rotated, and the bed 5 is moved in the direction of the body axis of the object P, moved in the direction of the radial axis of radiation, and moved in the direction of rotation to remain parallel with the installation surface of the radiotherapy unit 1 in order to match the isocenter of radiation with the location of the affected part by these movements (S01).

Secondly, the movable mechanism 24 is driven, and each pair of leaf blocks 23A and 23B is approached to or separated from each other (S02). The detecting element 25 detects displacement of each of the leaf blocks 23A or 23B targeted for detection (S03).

By accumulating information regarding detected displacement, the location of each of the leaf blocks 23A and 23B is specified (S04). The setup location of each of the leaf blocks 23A and 23B included in the treatment plan and the specified current location of each of the leaf blocks 23A and 23B are compared (S05), and if the current location does not reach the setup location (S06, No), return to S02, and each of the leaf blocks 23A and 23B will be further moved toward or separated from each other. If the current location reaches the setup location (S06, Yes), displacement of each of the leaf blocks 23A and 23B with the movable mechanism 24 is stopped (S07).

Subsequently, radiation is generated in the radiation source 21 with radiation dosage and emission time conforming to the treatment plan (S08), and emitted at the affected part of the object P.

Figure 6:
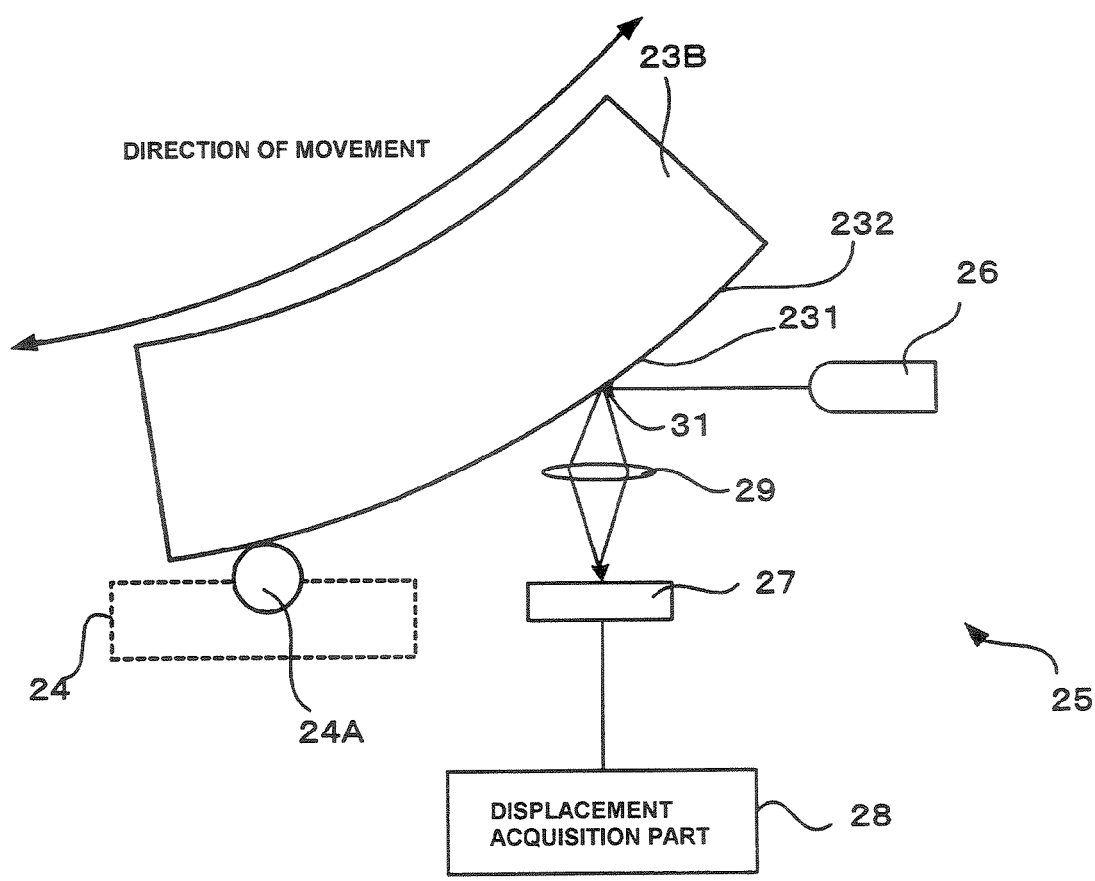
FIG. 6 is a side view of the multi-leaf collimator provided with the radiotherapy unit related to Embodiments 1 to 3 and Embodiment 5.
Figure 7:
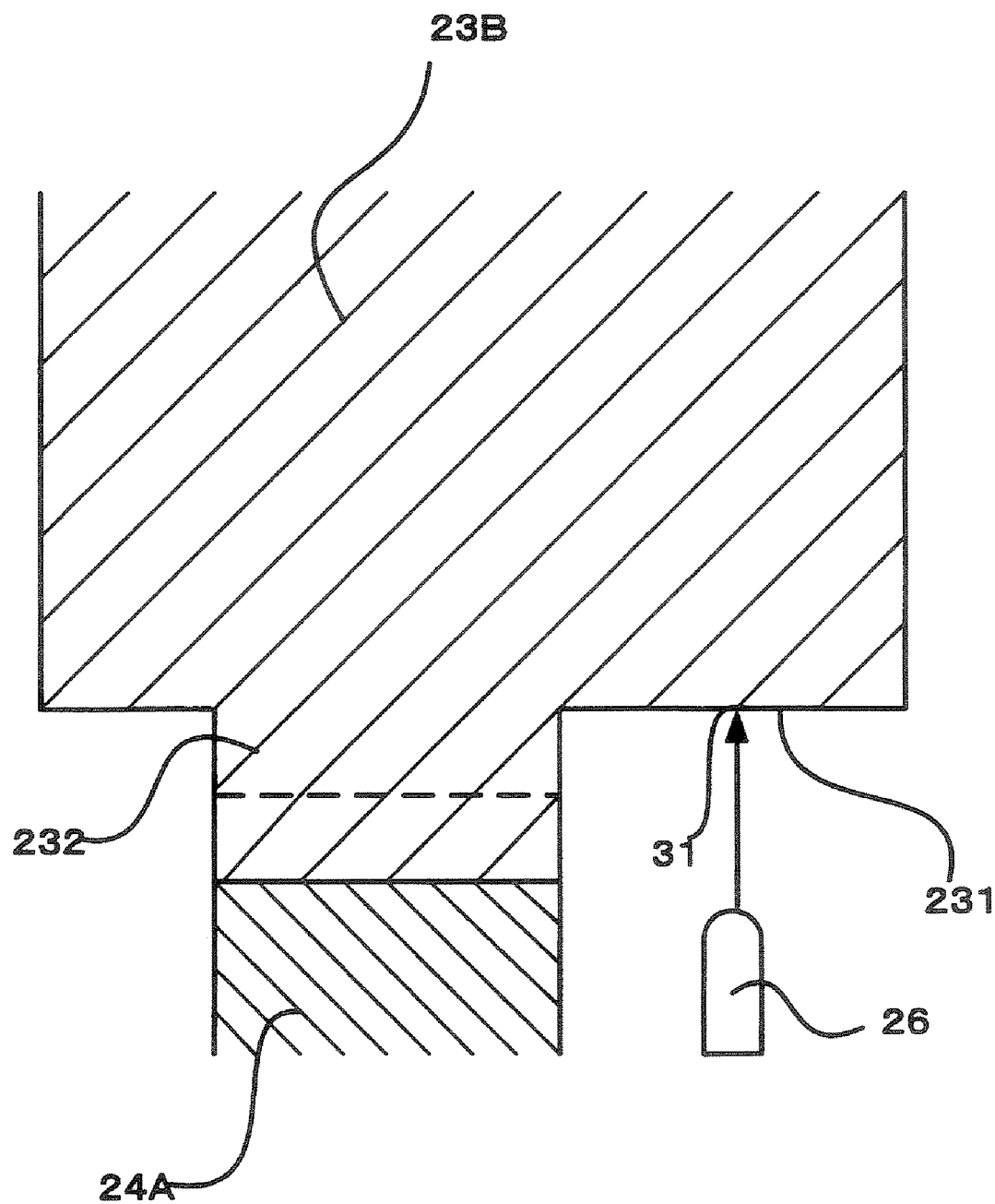
FIG. 7 is a sectional side view showing the periphery of the bottom surface of a leaf block provided with a radiotherapy unit related to Embodiments 1 to 5.

The multi-leaf collimator 23 of such a radiotherapy unit 1 will be described in further detail. FIG. 6 is a side view of the multi-leaf collimator 23, and FIG. 7 is a cross-sectional view of the leaf block 23B cut in the direction of the side surface, particularly showing the periphery around the bottom surface. Only the structure of the leaf blocks 23B is described below, as the structure of the leaf blocks 23A is the same.

As shown in FIG. 6 and FIG. 7, a toothed wheel cutting 232 is drawn along the longitudinal direction on the outer circumferential arc surface of the leaf block 23B. The movable mechanism 24 is provided with a drive motor and an output gear 24A. The toothed wheel cutting (gear cutting) 232 and output gear 24A engage with each other. Between the drive motor and output gear 24A, the drive power is transmitted from the drive motor to the output gear 24A through a plurality of gears.

The movable mechanism 24 rotates the multiple gears by activating the drive motor, and transmits drive power to the output gear 24A. This drive power rotates the output gear 24A. The leaf block 23B moves in the direction of movement to narrow or broaden the radiation field F along with rotation of the output gear 24A through engagement of the output gear 24A and the toothed wheel cutting 232.

Moreover, pattern images 231 are drawn along the longitudinal direction, or in other words along the direction of movement of the leaf block 23B, on the outer circumferential arc surface of the leaf block 23B. A plurality of the pattern images 231 are consecutively drawn. These pattern images 231 extend through the same range as the movable range of the leaf block 23B. In other words, the toothed wheel cutting 232 and pattern images 231 are drawn in parallel on the outer circumferential arc surface of the leaf block 23B.

The detecting element 25 is provided with an irradiation part 26 such as a light-emitting diode (diode), an image sensor 27 such as CCD, and displacement acquisition part 28 comprising a plurality of processing circuits or the like as shown in FIG. 6 and FIG. 7.

The irradiation part 26 irradiates a beam at a fixed point. The direction of irradiation from the irradiation part 26 is fixed, so the fixed point is an absolute location, independent from displacement of the leaf block 23B, and has a predetermined area. The irradiation part 26 sets the fixed point in the direction of the outer circumferential arc surface of the leaf block 23B so that the fixed point includes part of the region where the pattern images 231 are drawn.

The image sensor 27 performs fixed-point observations in the direction of the outer circumferential arc surface of the leaf block 23B at certain intervals. The observation point is the fixed point where the irradiation part 26 irradiates a beam. The image sensor 27 is subject to the beam reflected from this fixed point and acquires an image of fixed-point 31 at specified time intervals. The image of fixed-point 31 is an image in the fixed-point region. One of the pattern images 231 drawn on the leaf block 23B exists in the acquired image of fixed-point 31.

Furthermore, the detecting element 25 is provided with a lens 29 in an optical system between the fixed point and image sensor 27, aligning a scattering beam and adjusting magnification of images acquired by the image sensor 27.

The displacement acquisition part 28 analyzes the image of fixed-point 31 and acquires displacement of the leaf block 23B. If the leaf block 23B is displaced, the pattern images 231 drawn on the leaf block 23B will also move. The arranged locations of the pattern images 231 on the image of fixed-point 31 change according to displacement of the leaf block 23B. It recognizes the arranged locations of the pattern images 231, determines the difference between the arranged locations and acquires displacement of the arranged leaf block 23B from the differences of the arranged locations.

Figure 8:
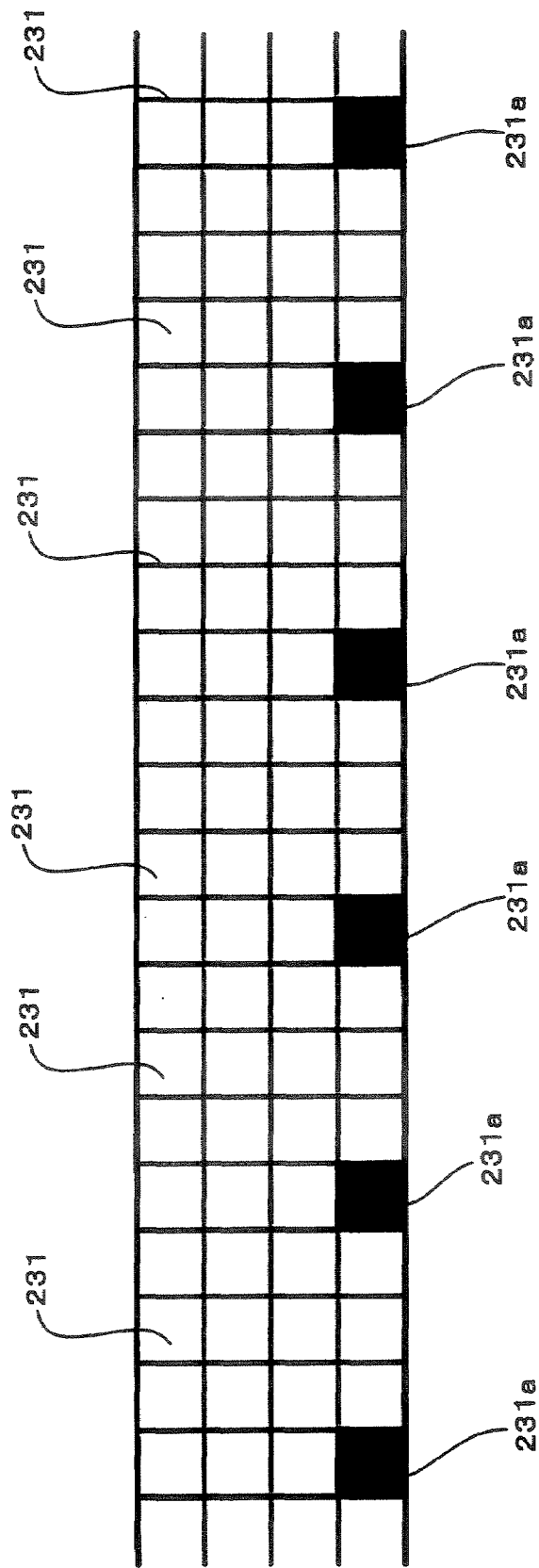
FIG. 8 is a view showing an example of pattern images drawn on a leaf block provided with a radiotherapy unit related to Embodiments 1 and 3 to 5.

FIG. 8 is a view showing an example of the pattern images 231 drawn on the leaf block 23B. As shown in FIG. 8, the pattern images 231 have predetermined marks, and a plurality of these are placed in consecutive lines. The patterns of pattern images 231 include specific patterns 231a that are in predetermined locations within the patterns. The specific patterns 231a are characteristic patterns that are different from patterns of other regions (including planes) of the pattern images 231.

The image sensor 27 captures fixed-point regions over time where the pattern images 231 are drawn. The specific patterns 231a of the pattern images 231 are included within the image of fixed-point 31. The displacement acquisition part 28 specifies the locations of specific patterns 231a placed within the image of fixed-point 31, and acquires displacement from the differences acquired over time. Therefore, regardless of the amount of displacement of the leaf block 23B at a certain time, it is preferable for some or all of the specific patterns 231a to exist within the image of fixed-point 31.

Thus, it is preferable for the size of the pattern images 231 to be smaller than that of the image of fixed-point 31.

The pattern images 231 have a specific pattern 231a carved deeper than the other segmented regions in predetermined segmented regions where, for example, an approximately 0.5-mm square region is divided into sixteen segments. For example, grating in the corner is the specific pattern 231a. The size of approximately 0.5 mm square is to be a region smaller than the fixed-point region observed by the image sensor 27. The patterns can be evenly carved, or can be carved by loose grooves.

Figure 9:
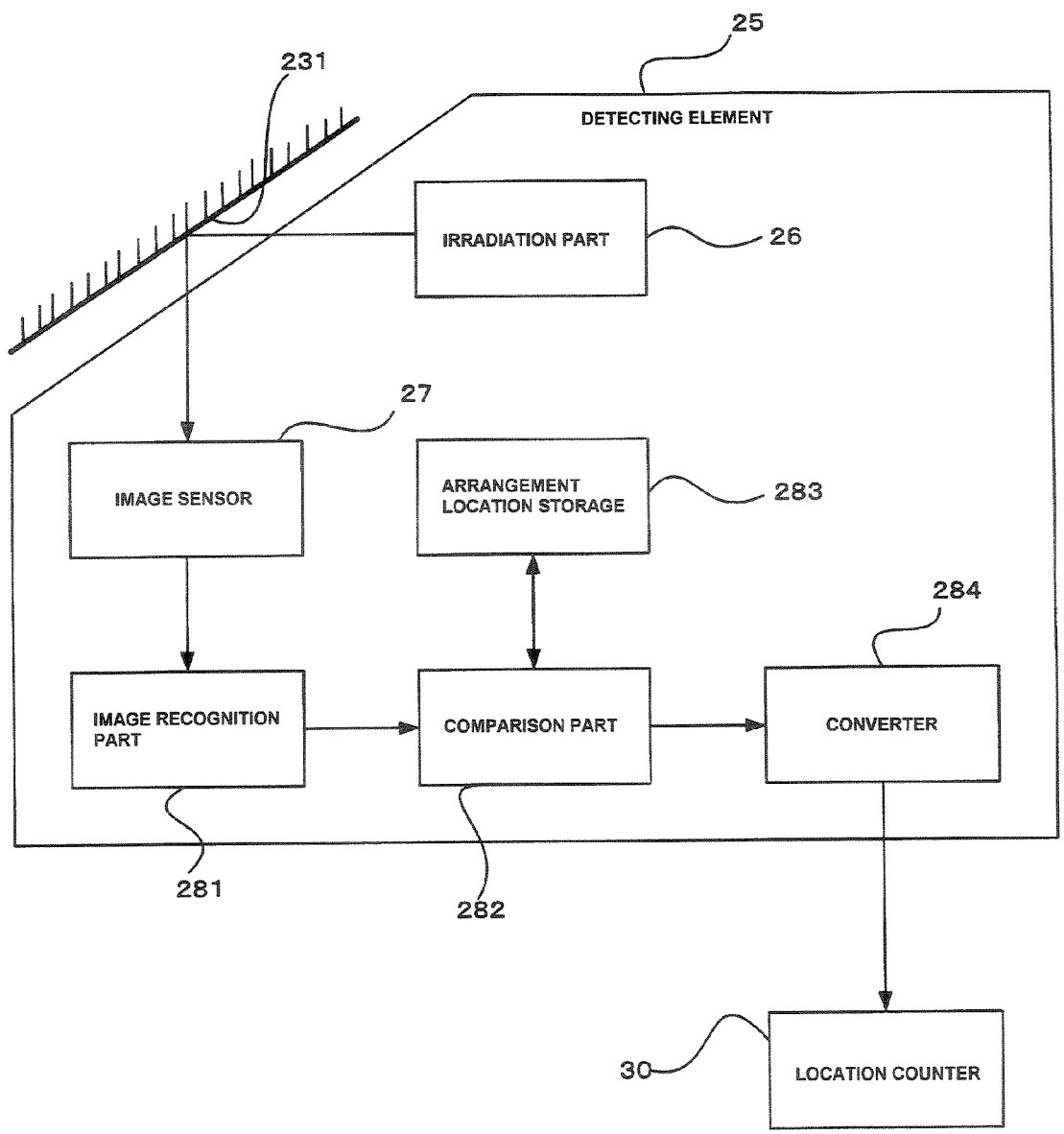
FIG. 9 is a block diagram showing the detecting element provided with a radiotherapy unit related to the Embodiments 1 and 3 to 5.

FIG. 9 is a block diagram showing the detecting element 25 in detail, particularly for describing the displacement acquisition part 28 in more detail. The displacement acquisition part 28 is provided with an image recognition part 281, comparison part 282, and converter 284.

The image recognition part 281 is electrically connected to the image sensor 27. The image of fixed-point 31 acquired by the image sensor 27 is input into the image recognition part 281. This image recognition part 281 scans the image of fixed-point 31 and recognizes the arranged locations of the pattern images 231 existing in the image.

In scanning the image of fixed-point 31, the specific patterns 231a that the pattern images 231 existing within the image of fixed-point 31 form are searched, and arrangement location information showing the arranged locations of the specific patterns 231a is acquired. The arrangement location information is shown in the coordinate range where the specific patterns 231a are located.

Furthermore, the leaf block 23B only moves one-dimensionally in a direction to narrow or broaden the radiation field F, so locations of the specific patterns 231a change one-dimensionally. Therefore, the image recognition part 281 can scan only the range of lines that may comprise the specific patterns 231a. Moreover, the arrangement location information can be information that shows the range of rows of coordinates where the specific patterns 231a are distributed.

The scanning process detects brightness shown by pixels in the scan range and extracts the coordinates of pixels with a specific luminance value shown by the specific patterns 231a. If the specific patterns 231a is deeply carved or consists of loose grooves, the brightness will be lower than that of the other regions.

The comparison part 282 acquires differences in pattern images 231 by comparing the arranged locations of the pattern images 231 existing in two images of fixed-point 31 that differ over time. The comparison part 282 and image recognition part 281 are electrically connected, and the arrangement location information is input into the comparison part 282 from the image recognition part 281.

This comparison part 282 is provided with an arrangement location storage 283 comprising a memory circuit. The arrangement location information for pattern images 231 existing in the previously acquired image of fixed-point 31 is stored in the arrangement location storage 283.

The comparison part 282 reads the previous arrangement location information stored in the arrangement location storage 283, differentiates it from the arrangement location information newly output by the image recognition part 281, and acquires information regarding the difference. Information regarding the difference shows differences in specific patterns 231a, including information for the direction of difference and amount of difference.

The differentiation process differentiates the arrangement location information newly input by the image recognition part 281 from the previous arrangement location information, and acquires the remaining coordinate range. Distribution of the remaining coordinate range shows the amount of difference, and the difference in values between the coordinate range shown by the arrangement location information acquired previously and the remaining coordinate range shows the direction of difference. A value of the remaining coordinate range that is smaller shows that the difference has moved in the direction of the pixels that takes a lower value for the row coordinate. The value of the coordinate range may, for example, be medial coordinates of each point of the coordinate range. The comparison part 282 creates information regarding the difference, including this amount of difference and direction of difference, and outputs it to the converter 284.

The converter 284 is electrically connected to the comparison part 282, with information regarding the difference input therein. This converter 284 has a conversion formula for converting information regarding the difference that shows displacement of pixel units into an actual displacement amount of the leaf block 23B. The input information regarding the difference is converted into actual displacement of the leaf block 23B with the conversion formula.

Furthermore, displacement of the leaf block 23B detected with the detecting element 25 is input into a location counter 30 provided with the radiotherapy unit 1. The location counter 30 comprises a data storage such as semiconductor memory, accumulatively adding displacement detected with the detecting element 25 and recording it therein. This location counter 30 can comprise a detecting element 25.

In the radiotherapy unit 1 of this embodiment, the leaf block 23B is moved to the default location by the movable mechanism 24 at the time of starting the apparatus when displacement starts to be recorded accumulatively, so the cumulative value of displacement shows the location of the leaf block 23B.

Figure 10:
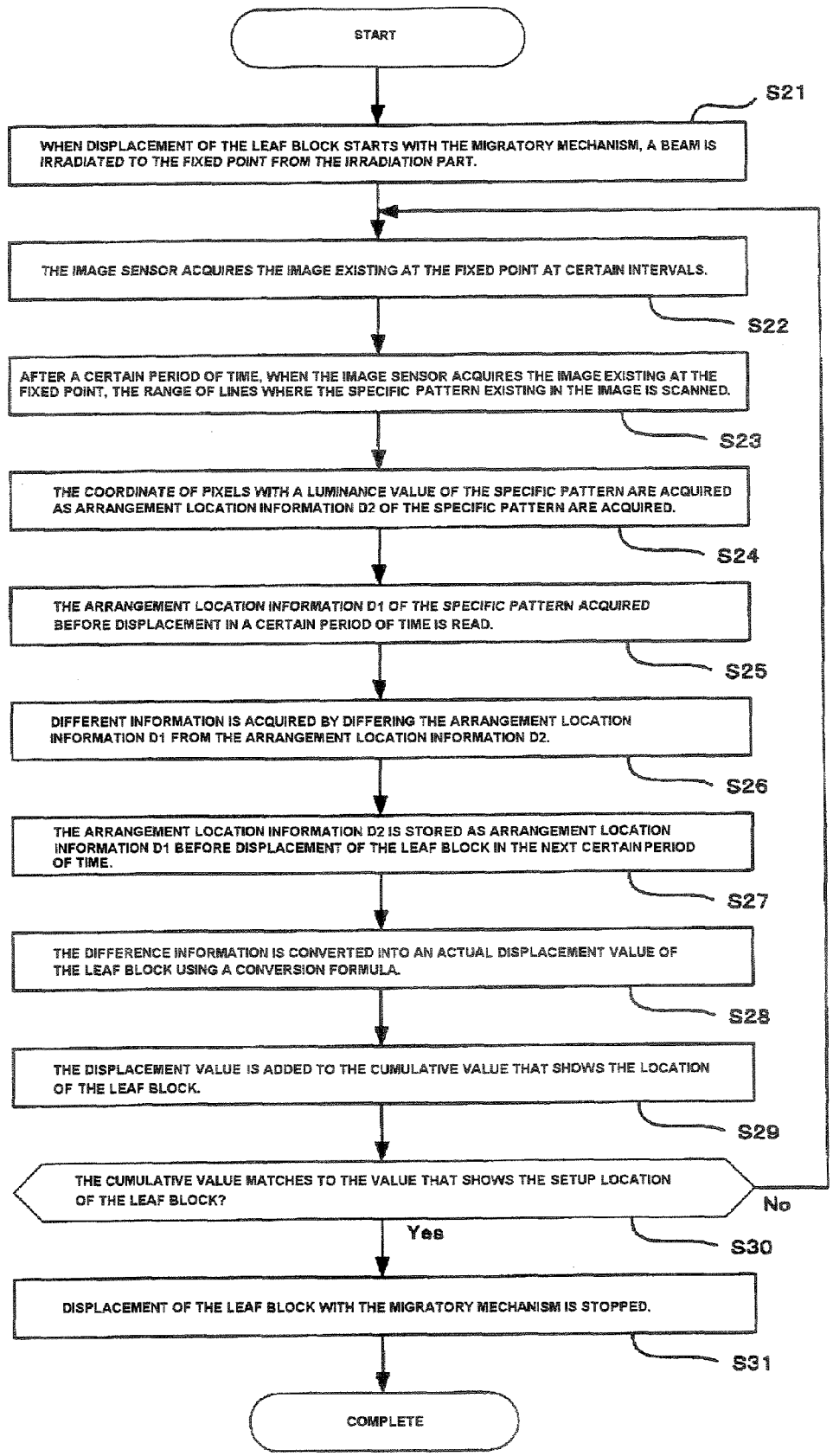
FIG. 10 is a flowchart showing displacement detection operation for leaf blocks provided with a radiotherapy unit related to Embodiments 1 and 3 to 5.
Figure 11A:
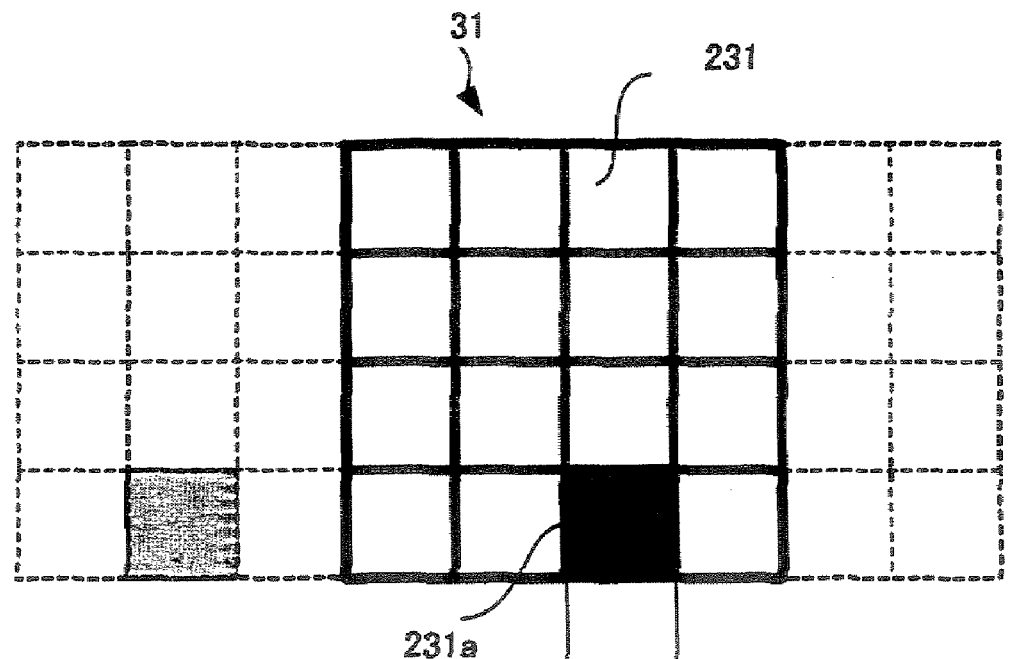
FIG. 11 is a view showing consecutive images of fixed-point over time captured by an image sensor provided with a radiotherapy unit related to Embodiments 1 and 3 to 5, with (a) being an image of fixed-point before displacement of a leaf block and (b) being an image of fixed-point after displacement of a leaf block during that period.
Figure 11B:
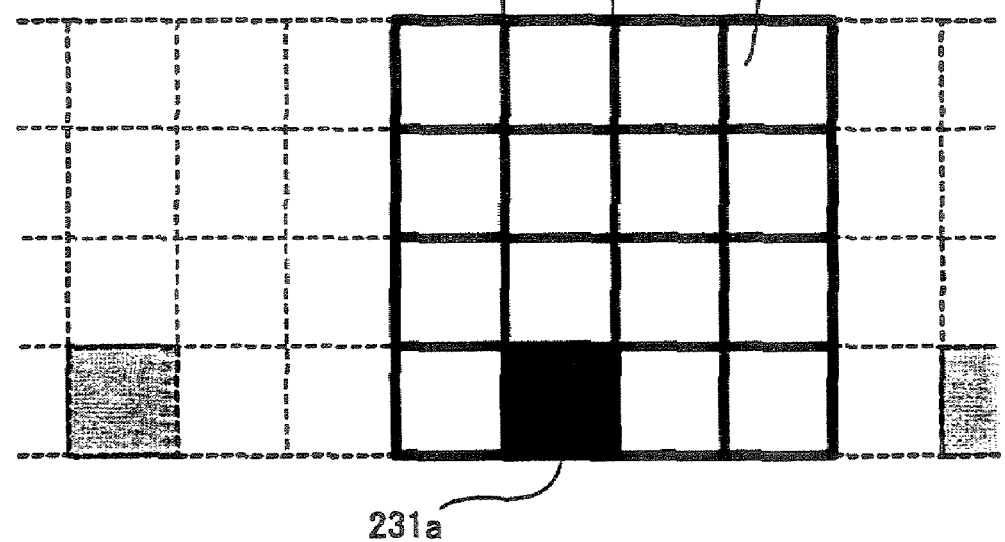

Based on FIG. 10 and FIG. 11, the detection operation for displacement of the leaf block 23B of this radiotherapy unit 1 will be described. FIG. 10 is a flow chart showing the detection operation for displacement of the leaf block 23B. FIG. 11 is a view showing the consecutive images of fixed-point 31 over time captured by the image sensor 27 at a certain period of time, with (a) being the image of fixed-point 31a before displacement of the leaf block 23B at that period of time and (b) being the image of fixed-point 31b after displacement of the leaf block 23B.

First, when displacement of the leaf block 23B starts with the movable mechanism 24, a beam is irradiated at the fixed point from the irradiation part 26 (S21), and the image sensor 27 acquires the images of fixed-point 31 existing at the fixed point at certain intervals (S22).

Herein, the image sensor is supposed to acquire the image of fixed-point 31 before displacement of the leaf block 23B at a certain period of time. The image recognition part 281 recognizes the arranged locations of the pattern images 231 existing in the image of fixed-point 31a before this displacement, acquiring arrangement location information D1 of the specific pattern 231a. This arrangement location information D1 is stored in the arrangement location storage 283.

Secondly, after displacement of the leaf block 23B at that certain period of time, when the image sensor 27 acquires the image of fixed-point 31b existing at the fixed point, the image recognition part 281 scans the range of lines where the specific pattern 231a existing in the image of fixed-point 31b is placed (S23).

While scanning, the image of fixed-point 31b finds pixels with a luminance value of the specific pattern 231a, the coordinates of the pixels are acquired as arrangement location information D2 of the specific pattern 231a (S24).

The comparison part 282 reads the arrangement location information D1 from the arrangement location storage 283 (S25). When the arrangement location information D1 is read, the arrangement location information D1 is differentiated from the arrangement location information D2 to acquire the difference (S26). In the displacement shown in FIG. 11, this difference creates information regarding the difference indicating that the specific pattern has moved to the left by a coordinate range D3.

When information regarding the difference is created, the arrangement location information D2 of the specific pattern 231 acquired after the displacement is updated and stored in the arrangement location storage 283 as arrangement location information D1 before displacement in the next period of time (S27).

Moreover, when information regarding the difference is acquired, the converter 284 converts this information regarding the difference into an actual displacement value for the leaf block 23B using the conversion formula (S28). The displacement value is output to the location counter 30 and is added to the cumulative value showing the location of the leaf block 23B stored by the location counter 30 (S29).

If the cumulative value showing the location of the leaf block 23B does not match the value showing the intended setup location of the leaf block 23B (S30, No), S23 to S31 are repeated to detect the difference by comparing the arranged locations of the pattern images 231 between the new image of fixed-point 31b after displacement and the previous image of fixed-point 31a.

If the cumulative value showing the location of the leaf block 23B matches the value showing the intended location of the leaf block 23B (S30, Yes), displacement of the leaf block 23B with the movable mechanism 24 is stopped (S31).

As described above, in the radiotherapy unit 1 of this embodiment, displacement of leaf block 23B can be detected without making contact, preventing displacement detection errors due to the effect of backlash and gear wear. Therefore, locations of the leaf blocks 23B can be detected with high precision, and the radiation field F can be matched with the shape of the affected part with high precision.

Embodiment 2

Next, Embodiment 2 of the radiotherapy unit 1 of the present invention will be described. Furthermore, the same codes are used for the same structures and same functions as in Embodiment 1, so detailed descriptions are omitted. The radiotherapy unit 1 of this embodiment detects the location of the leaf block 23B with the detecting element 25.

Figure 12:
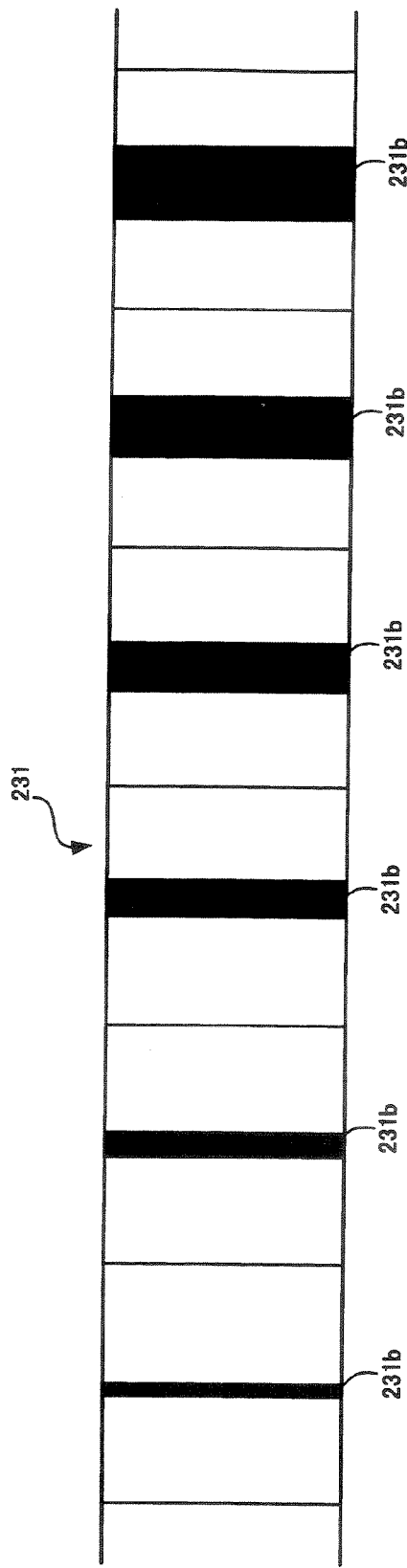
FIG. 12 is a view showing an example of pattern images drawn on a leaf block provided with a radiotherapy unit related to Embodiments 2 to 5.

FIG. 12 is a view showing the pattern image 231 drawn on the outer circumferential arc surface of the leaf block 23B. In the radiotherapy unit 1 of this embodiment, one pattern image 231 is drawn along the longitudinal direction, or in other words along the direction of movement of the leaf block 23B, on the outer circumferential arc surface of the leaf block 23B. The pattern image 231 is extended across the same width as the movable range of the leaf block 23B.

This pattern image 231 has a plurality of location-specific patterns 231b in parallel at predetermined intervals. These location-specific patterns 231b express location-specific patterns. "Location-specific" indicates that a pattern has different characteristics depending on the location where it is placed. The location-specific patterns 231b of this embodiment are striped and have a predetermined width, with the width of the strip varying, depending on the sequence location.

Figure 13:
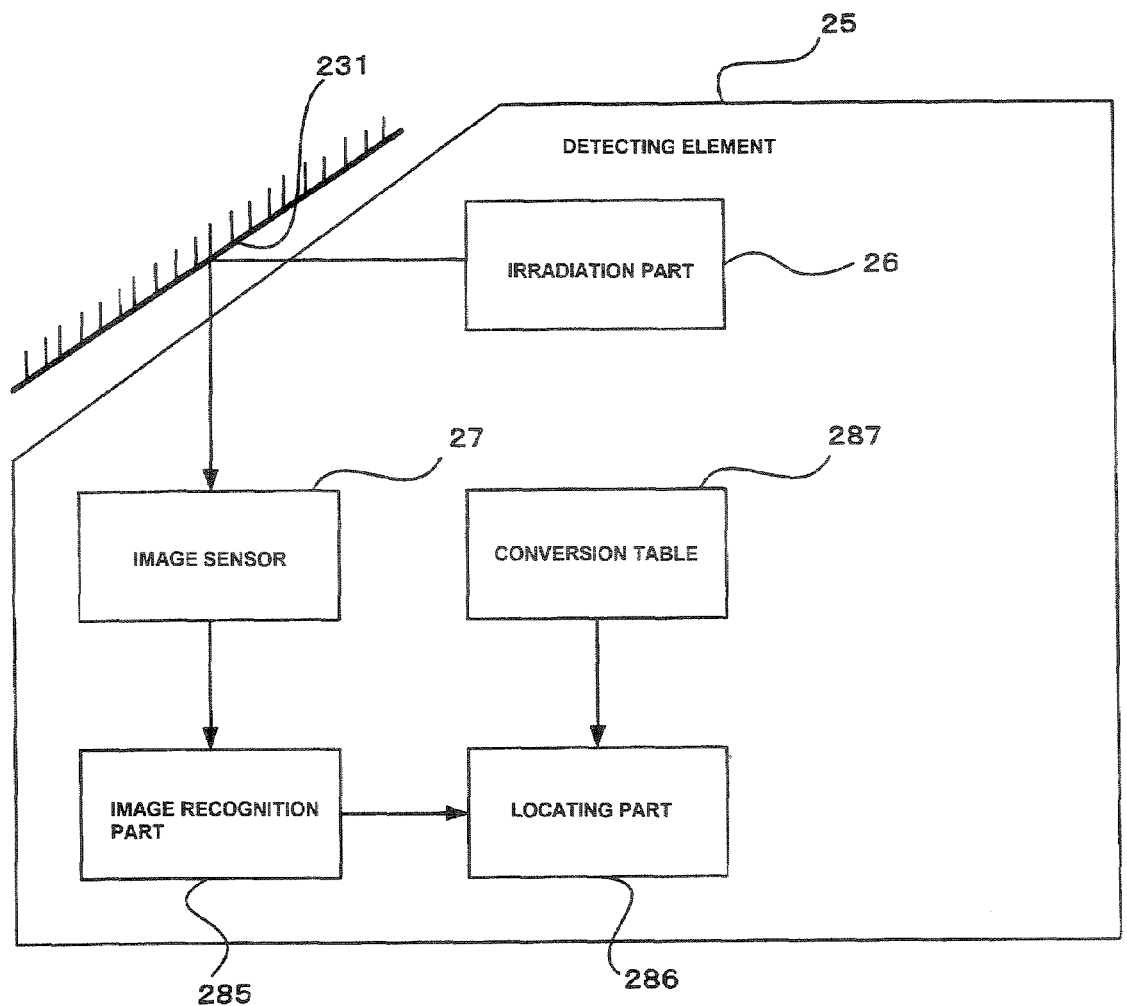
FIG. 13 is a block diagram of a detecting element provided with a radiotherapy unit related to Embodiments 2 to 5.

FIG. 13 is a block diagram showing the detecting element 25 that detects the location of the leaf block 23B. As shown in FIG. 13, the detecting element 25 is provided with the irradiation part 26, the image sensor 27, an image recognition part 285, and a locating part 286.

The image recognition part 285 is electrically connected to the image sensor 27, and the image of fixed-point 31 acquired by the image sensor 27 is input into it. This image recognition part 281 scans the image of fixed-point 31 and recognizes the location of the arranged pattern images 231 existing in the image.

While scanning the image of fixed-point 31, the location-specific patterns 231b of the pattern images 231 existing within the image of fixed-point 31 are searched, and arrangement location information of the location-specific patterns 231b is acquired. The arrangement location information is shown in a coordinate range where the location-specific patterns 231b exist.

The acquired arrangement location information includes information for the width of the location-specific patterns 231b existing within the image of fixed-point 31 according to the distribution width of the coordinate shown by this arrangement location information, in addition to the information for locations of the arranged location-specific patterns 231b. That is to say, the arrangement location information includes information to specify the location-specific patterns and information for the arrangement locations within the image of fixed-point 31.

This scanning is performed only on the range of lines that possibly comprises the location-specific patterns 231b. The scanning process extracts a coordinates of pixels with a specific luminance value shown by the location-specific patterns 231b. The arrangement location information can be information that shows the range of rows of the coordinate where the location-specific patterns 231b are distributed.

The locating part 286 specifies the location of the leaf block 23B from the arrangement location information. This locating part 286 is provided with a conversion table (table) 287 comprising a memory circuit. In the conversion table 287, information for the width of the location-specific patterns 231b and information for the location of the leaf block 23B are stored in pairs.

The information for the location of the leaf block 23B is information that shows the location of the leaf block 23B when the location-specific patterns 231b corresponding to the paired information for width is located in the center of the image of fixed-point 31.

Locating the leaf block 23B consists of a specific process for the pattern of the location-specific patterns 231b existing within the image of fixed-point 31, a tentative specific process for the location of the leaf block 23B, a process for calculating the difference between the center of the image of fixed-point 31 and the location-specific patterns 231b, and a final locating process for the tentatively specified location of the leaf block 23B.

In the specific process for the pattern and the tentative specific process for the location, once the arrangement location information is input, the locating part 286 acquires the distribution width of the coordinate from the arrangement location information, searches information from the conversion table 287 for the width that matches the distribution width, and acquires the location information.

In the process of calculating the difference, the locating part 286 calculates the difference between the center coordinates of the image of fixed-point 31 preliminarily stored by the locating part 286 and the medial coordinates of the coordinate range shown by the arrangement location information.

In the final locating process, the locating part 286 adds the difference calculated in the process of calculating the difference to the acquired information for the locations. The result of adding the difference to this information for the location is led to the precise location of the leaf block 23B.

Figure 14:
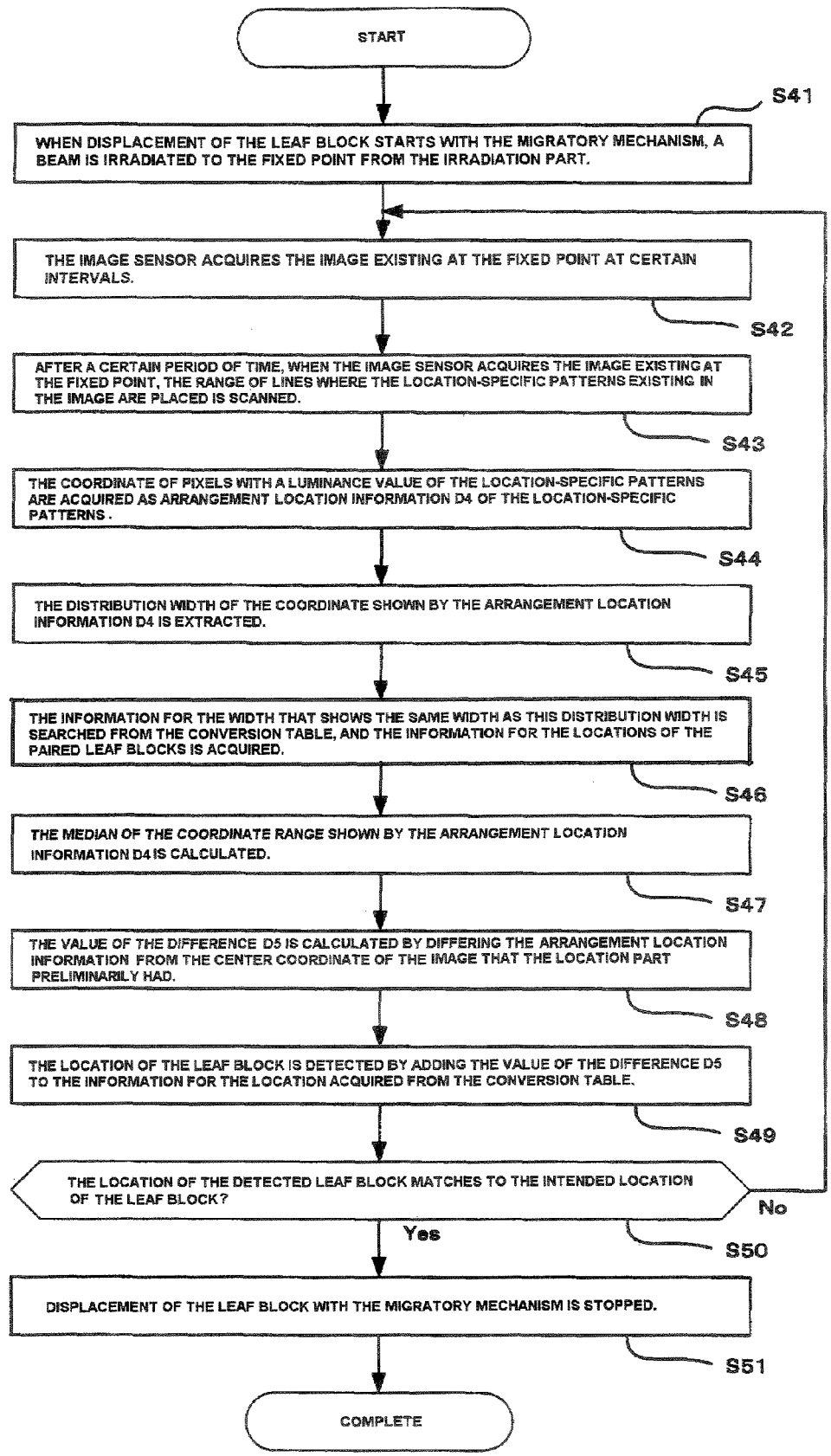
FIG. 14 is a flowchart showing displacement detection operation for a leaf block provided with a radiotherapy unit related to Embodiments 2 to 5.
Figure 15:
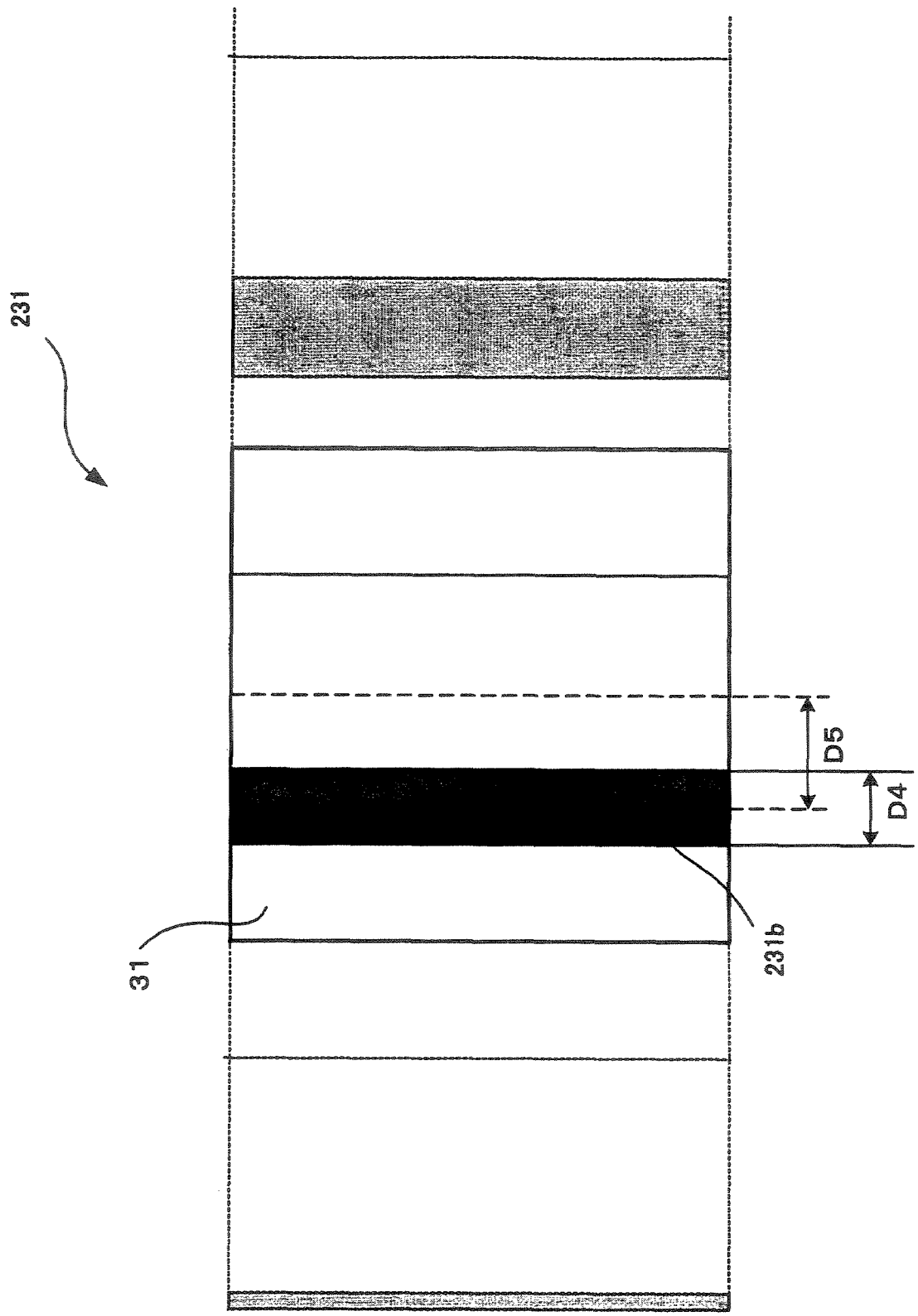
FIG. 15 is a view showing an image of fixed-point captured by an image sensor provided with a radiotherapy unit related to Embodiments 2 to 5.

The detection operation for the location of the leaf block 23B regarding the radiotherapy unit 1 related to this embodiment will be described based on FIG. 14 and FIG. 15.

First, when displacement of the leaf block 23B starts with the movable mechanism 24, a beam is irradiated at the fixed point from the irradiation part 26 (S41), and the image sensor 27 acquires the images of fixed-point 31 existing at the fixed point at certain intervals (S42).

Secondly, after displacement of the leaf block 23B at a certain period of time, when the image sensor 27 acquires the image of fixed-point 31b existing at the fixed point, the image recognition part 281 scans the range of lines where the location-specific patterns 231b existing in the image of fixed-point 31 are placed (S43).

When scanning the image of fixed-point 31 finds pixels with a luminance value of the location-specific patterns 231b, the coordinates of the pixels are acquired as arrangement location information D4 of the location-specific patterns 231b (S44).

The locating part 286 extracts the distribution width of the coordinate shown by the arrangement location information D4 (S45), searches the information for the width that shows the same width as this distribution width from the conversion table 287, and acquires the information for the location of the paired leaf blocks 23B (S46).

Moreover, the locating part 286 calculates the median of the coordinate range shown by the arrangement location information D4 (S47), and calculates the value of the difference D5 By differing the arrangement location information D4 from the center coordinates of the image of fixed-point 31 that the locating part 286 previously had (S48). The location when the image of fixed-point 31 of the leaf block 23B was acquired is detected by adding the value of the difference D5 to the information for the location acquired from the conversion table 287 (S49).

When the acquired location of the leaf block 23B matches the intended location of the leaf block 23B (S50, Yes), displacement of the leaf block 23B with the movable mechanism 24 is stopped (S51).

As described above, in the radiotherapy unit 1 of this embodiment, the location of leaf block 23B can be detected without making contact, and location detection errors due to the effect of backlash and gear wear can be prevented. Therefore, locations of the leaf blocks 23B can be detected with high precision, and the radiation field F can be matched to the shape of the affected part with high precision.

Embodiment 3

Next, Embodiment 3 of the radiotherapy unit 1 of the present invention will be described. The same codes are used for the same structures and same functions as Embodiments 1 and 2, so detailed descriptions are omitted. The radiotherapy unit 1 of this embodiment detects displacement and detects locations in a similar manner as in Embodiments 1 or 2.

FIG. 16 is a view showing locations of the arranged irradiation part 26 and the image sensor 27. In the radiotherapy unit 1 of this embodiment, a pair of the irradiation part 26 and the image sensor 27 for detecting the displacement or location of the same leaf block 23B and a pair of the irradiation part 26 and the image sensor 27 corresponding to the adjacent leaf block 23B, are differently arranged in lines.

Figure 16A:
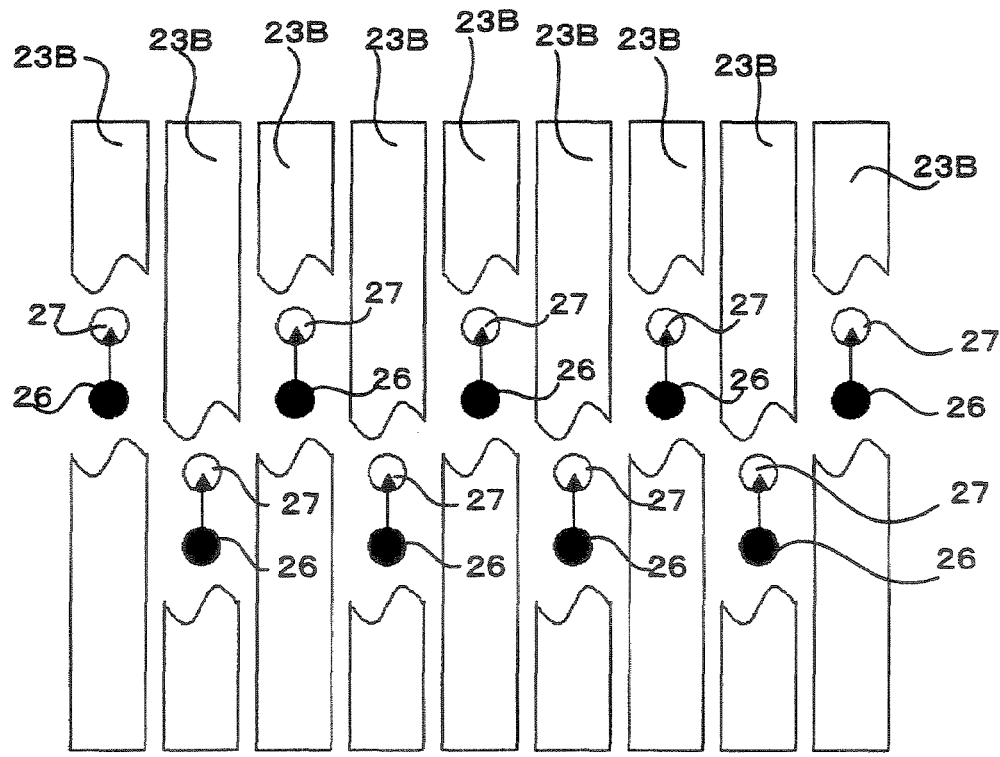
FIG. 16 is a view showing the arranged locations of irradiation parts and image sensors provided with a radiotherapy unit related to Embodiment 3.

As shown in FIG. 16(a), for example, pairs of the irradiation parts 26 and the image sensors 27 corresponding to each of the leaf blocks 23B are arranged alternately in two lines so that the adjacent pairs of the irradiation parts 26 and the image sensors 27 do not belong to the same lines.

Figure 16B:
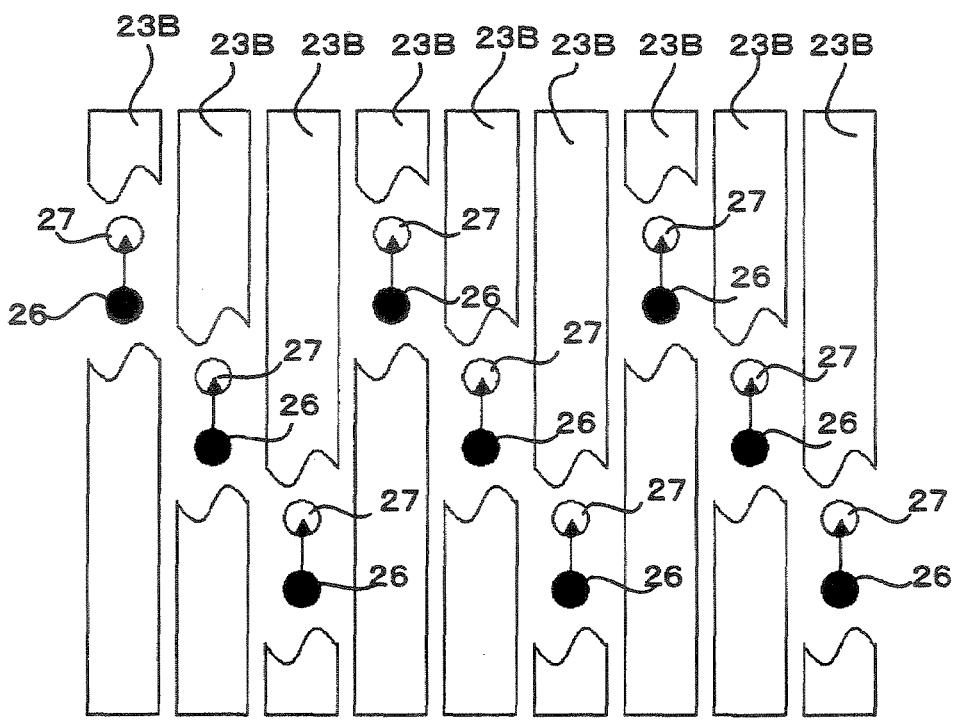

Furthermore, as shown in FIG. 16(b), for example, pairs of the irradiation parts 26 and the image sensors 27 corresponding to each of the leaf blocks 23B are arranged in three lines so that pairs of the irradiation parts 26 and the image sensors 27 respectively corresponding to the three leaf blocks 23B aligned in sequence all belong to different lines.

In order to more precisely match the radiation field F created by the multi-leaf collimator 23 with the shape of the affected part, it is preferable for the thickness of the leaf blocks 23A and 23B to be thinner and for more pairs of leaf blocks 23A and 23B to be placed.

In the radiotherapy unit 1 of this embodiment, the adjacent pairs of the irradiation parts 26 and the image sensors 27 are differently arranged in lines, so when a certain irradiation part 26 irradiates radiation, the adjacent image sensors 27 are not subject to any of the borrowed light reflected on the leaf blocks 23B.

This enables the acquisition of a clear image of fixed-point 31 without noise in the image of fixed-point 31 acquired by the image sensors 27, enhancing the accuracy of the arrangement location information acquired by the image recognition part 281 or 285, and detecting the displacement or locations of the leaf blocks 23B with higher accuracy.

Embodiment 4

Next, Embodiment 4 of the radiotherapy unit 1 of the present invention will be described. The same codes are used for the same structures and same functions as in Embodiments 1 and 2, so detailed descriptions are omitted. The radiotherapy unit 1 of this embodiment detects displacement and locations in a similar way to Embodiments 1 or 2. The radiotherapy unit 1 of this embodiment is a modified example of improvement in accuracy of the arrangement location information related to Embodiment 3.

Figure 17:
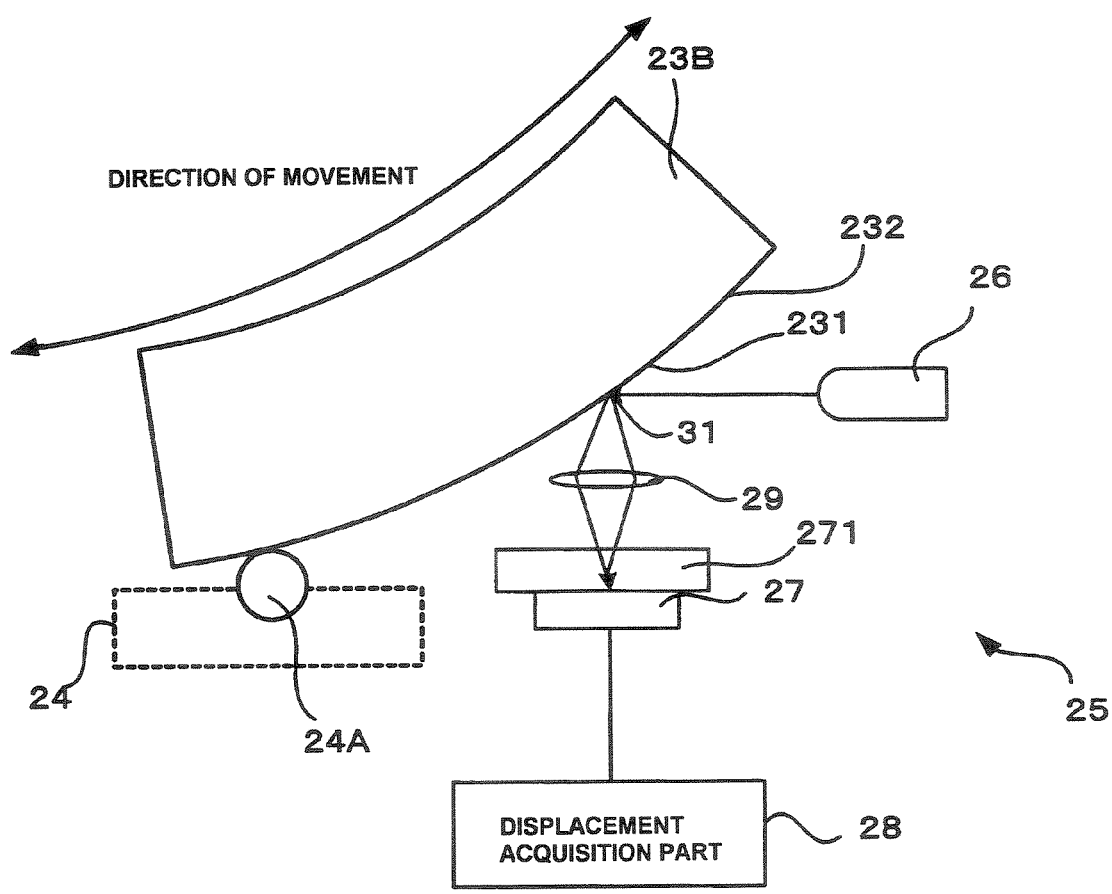
FIG. 17 is a side view of a leaf block provided with a radiotherapy unit related to Embodiment 4.

FIG. 17 is a side view of the leaf block 23B in this embodiment. The irradiation part 26 placed corresponding to each of the leaf blocks 23B irradiates a beam with a wavelength different from the wavelength of the beam irradiated by the adjacent irradiation part 26.

The detecting element 25 is provided with an optical filter (filter) 271 in the optical filter between the irradiation part 26 and the image sensor 27. This optical filter 271 only transilluminates a beam with a specific wavelength. The beam with a specific wavelength that is transilluminatable is a beam with a wavelength irradiated by the irradiation part 26 that forms the optical system where the optical filter 271 is placed. This beam irradiated by the irradiation part 26 is transilluminated, and other beams irradiated from the other irradiation parts 26 are absorbed and not transilluminated.

In such detecting element 25, the optical filter 271 placed in the optical system formed by the predetermined irradiation part 26 transilluminates a beam with a specific wavelength irradiated by this predetermined irradiation part 26, and has the image sensor 27 subject to the beam.

At the same time, when a beam irradiated by the irradiation part 26 placed corresponding to the adjacent leaf blocks 23B enters by scattering on the surface of the adjacent leaf blocks 23B, the optical filter 271 absorbs this beam and does not transilluminate it in the direction of the image sensor 27.

This enables the acquisition of a clear image of fixed-point 31 without noise in the image of fixed-point 31 acquired by the image sensors 27, enhancing the accuracy of the arrangement location information acquired by the image recognition part 281 or 285, and detecting the displacement or locations of the leaf blocks 23B with higher accuracy.

Embodiment 5

Next, Embodiment 5 of the radiotherapy unit 1 of the present invention will be described. The same codes are used for the same structures and same functions as in Embodiments 1 and 2, so detailed descriptions are omitted. The radiotherapy unit 1 of this embodiment detects the displacement and locations in a similar manner to Embodiment 1 or 2. The radiotherapy unit 1 in this embodiment is a modified example of improvement in accuracy of the arrangement location information related to Embodiment 3.

Figure 18:
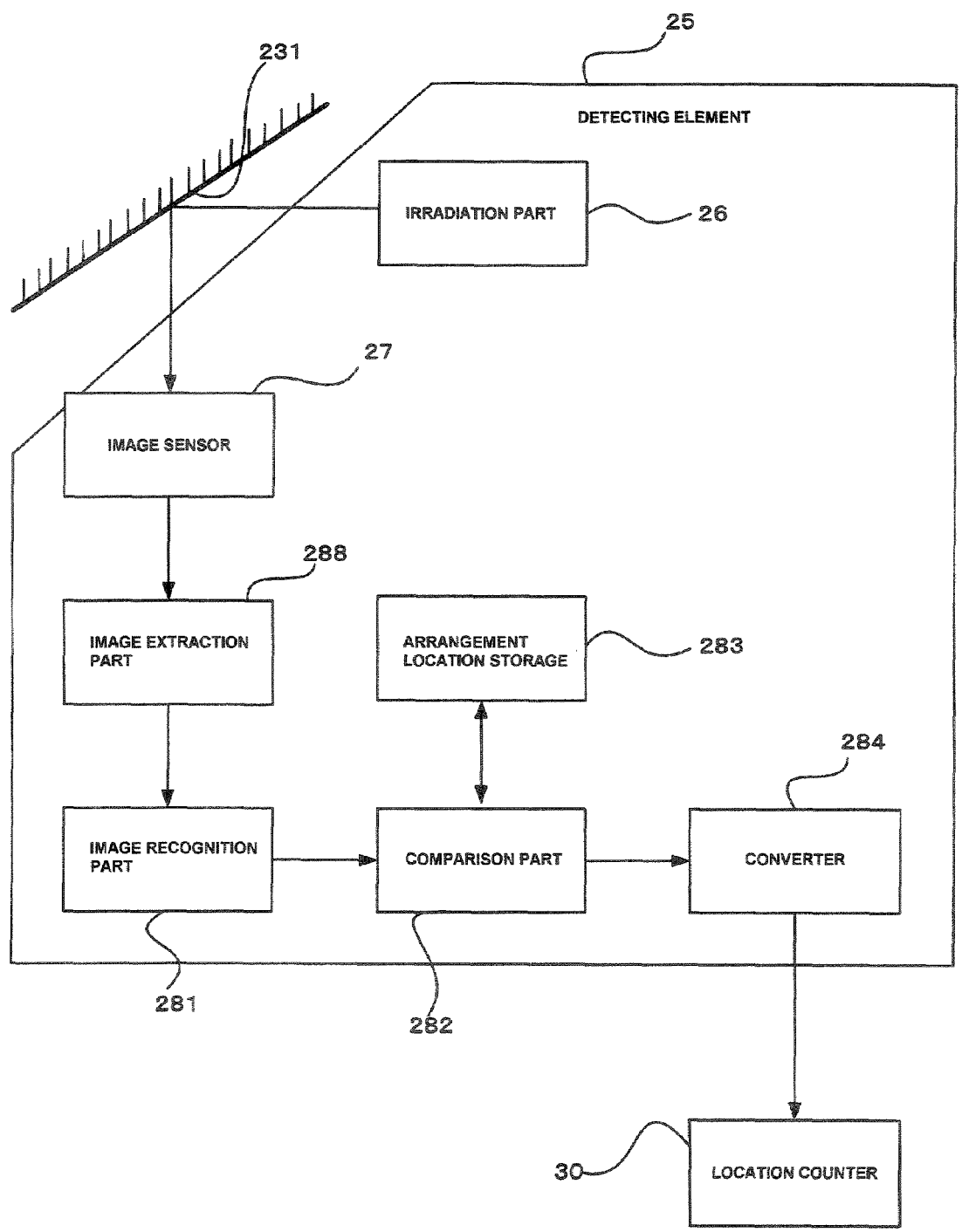
FIG. 18 is the block diagram of a detecting element provided with a radiotherapy unit related to Embodiment 5.

FIG. 18 is a block diagram of a detecting element 25 in this embodiment. The irradiation part 26 placed corresponding to each of the leaf blocks 23B irradiates a beam with a wavelength different from the wavelength of beams irradiated by the adjacent irradiation parts 26.

The detecting element 25 is provided with an image extraction part 288 electrically connected between the image sensor 27 and the image recognition part 281 (or 285). The image extraction part 288 extracts only the signal of an image based on a beam with a unique wavelength of the irradiation part 26 placed correspondingly from the image of fixed-point 31 acquired by the image sensor 27 placed correspondingly in the same way. Signals of images converted by the image sensor 27 subject to beams irradiated by the adjacent irradiation parts 26 are eliminated by this image extraction part 288.

This enables the acquisition of a clear image of fixed-point 31 without pattern images drawn on the adjacent leaf blocks 23B in the image of fixed-point 31 being input into the image recognition part 281 (or 285), thereby enhancing the accuracy of the arrangement location information acquired by the image recognition parts 281 or 285, and detecting the displacement or locations of the leaf blocks 23B with higher accuracy.

What is claimed is:

1. A multi-leaf collimator that narrows a radiation field to a predetermined shape comprising:
   leaf blocks movable in the direction of scaling the radiation field and having a pattern drawn along the direction of movement on a predetermined surface; and
   a detection part configured to acquire images of the pattern included in a region along said predetermined surface and to detect displacement of said leaf blocks based on a temporal change of said images.

2. A multi-leaf collimator according to claim 1, wherein said pattern has specific markings at predetermined locations, and
   said detection part specifies the arranged locations of said pattern according to said specific markings.

3. A multi-leaf collimator according to claim 1, wherein said detection part comprises:
   a radiation part irradiating a beam in the direction of said predetermined surface;
   image sensors subject to light reflected from the direction of said predetermined surface and acquiring said images; and
   a displacement acquisition part acquiring displacement of said leaf blocks from the pattern existing in said images.

4. The multi-leaf collimator according to claim 3, wherein said displacement acquisition part comprises:
   a recognition part recognizing the arranged locations of the pattern existing in said images; and
   a comparison part acquiring differences between images of the pattern by comparing the arranged locations of the pattern existing in an image acquired previously and the arranged locations of the pattern existing in an image currently acquired, wherein,
   displacement of said leaf blocks is acquired from said difference.

5. A multi-leaf collimator according to claim 3, wherein a plurality of said leaf blocks is arranged in parallel, and
   said radiation part and said image sensors placed corresponding to predetermined leaf blocks and said radiation part and said image sensors placed corresponding to other leaf blocks adjacent to the predetermined leaf blocks, are differently arranged in line at the locations of placement.

6. A multi-leaf collimator according to claim 3, wherein a plurality of said leaf blocks is arranged in parallel,
   a plurality of said radiation parts are placed corresponding to each leaf block in pairs,
   a plurality of said image sensors are placed corresponding to said radiation part in pairs,
   said radiation part irradiates a beam with a wavelength different from that of said radiation part corresponding to the other leaf blocks adjacent to corresponding leaf blocks, and
   said image sensors are provided with filters for transilluminating a beam with a wavelength irradiated by a pair of said radiation part.

7. A multi-leaf collimator according to claim 3, wherein a plurality of said leaf blocks is arranged in parallel,
   a plurality of said radiation parts are placed corresponding to each leaf block in pairs,
   a plurality of said image sensors are placed corresponding to said radiation part in pairs,
   said radiation part irradiates a beam with a wavelength different from that of said radiation part corresponding to the other leaf blocks adjacent to corresponding leaf blocks, and
   said detection part further comprises an extraction part acquiring images obtained by irradiation of the radiation part, by extracting only images created by a beam with a wavelength irradiated by said radiation part paired with the image sensors.

8. A multi-leaf collimator that narrows a radiation field to a predetermined shape comprising:
   leaf blocks movable in the direction of scaling the radiation field and having a pattern drawn along the direction of movement on a predetermined surface; and
   a detection part configured to acquire images of the pattern included in a region along said predetermined surface and to detect locations of said leaf blocks based on a temporal change of said images.

9. A multi-leaf collimator according to claim 8, wherein said pattern has location-specific markings in parallel along a drawing area, and
   said detection part specifies the arranged locations of said pattern according to said location-specific markings.

10. A multi-leaf collimator according to claim 8, wherein said detection part comprises:
    a radiation part irradiating a beam in the direction of said predetermined surface;
    image sensors subject to light reflected from the direction of said predetermined surface and acquiring said images; and
    a location acquisition part acquiring the locations of said leaf blocks from the pattern existing in said images.

11. A multi-leaf collimator according to claim 10, wherein said location acquisition part comprises:
    a recognition part recognizing the arranged locations of the pattern existing in said images, wherein,
    the locations of said leaf blocks are acquired according to the arranged locations of said pattern.

12. A multi-leaf collimator according to claim 10, wherein a plurality of said leaf blocks is arranged in parallel, and
    said radiation part and said image sensors placed corresponding to predetermined leaf blocks and said radiation part and said image sensors placed corresponding to the other leaf blocks adjacent to the predetermined leaf blocks, are differently arranged in line at the locations of placement.

13. A multi-leaf collimator according to claim 10, wherein a plurality of said leaf blocks is arranged in parallel,
   a plurality of said radiation parts are placed corresponding to each leaf block in pairs,
   a plurality of said image sensors are placed corresponding to said radiation part in pairs,
   said radiation part irradiates a beam with a wavelength different from that of said radiation part corresponding to the other leaf blocks adjacent to corresponding leaf blocks, and
   said image sensors are provided with filters for transilluminating a beam with a wavelength irradiated by a pair of said radiation part.

14. A multi-leaf collimator according to claim 10, wherein a plurality of said leaf blocks is arranged in parallel,
   a plurality of said radiation parts are placed corresponding to each leaf block in pairs,
   a plurality of said image sensors are placed corresponding to said radiation part in pairs,
   said radiation part irradiates a beam with a wavelength different from that of said radiation part corresponding to the other leaf blocks adjacent to corresponding leaf blocks, and
   said detection part further comprises an extraction part acquiring an image obtained by irradiation from the radiation part, by extracting only images created by a beam with a wavelength irradiated by said radiation part paired with the image sensors.

15. A radiotherapy unit comprising:
   a radiation source for irradiating radiation;
   a bed on which to place an object; and
   a multi-leaf collimator between said radiation source and said bed, narrowing a radiation field to a predetermined shape, said multi-leaf collimator comprising:
      leaf blocks movable in the direction of scaling the radiation field and having a pattern drawn along the direction of movement on a predetermined surface; and
      a detection part configured to acquire images of the pattern included in a region along said predetermined surface and to detect displacement of said leaf blocks based on a temporal change of said images.

16. A radiotherapy unit according to claim 15, wherein said pattern has specific markings at predetermined locations, and
   said detection part specifies the arranged locations of said pattern according to said specific markings.

17. A radiotherapy unit according to claim 15, wherein said detection part comprises:
   a radiation part irradiating a beam in the direction of said predetermined surface;
   image sensors subject to light reflected from the direction of said predetermined surface and acquiring said images; and
   a displacement acquisition part acquiring displacement of said leaf blocks from the pattern existing in said images.

18. A radiotherapy unit according to claim 17, wherein said displacement acquisition part comprises:
   a recognition part recognizing the arranged locations of the pattern existing in said images; and
   a comparison part acquiring the difference between images of the pattern by comparing the arranged locations of the pattern existing in an image acquired previously and the arranged locations of the pattern images existing in an image currently acquired, and acquiring displacement of said leaf blocks from said difference.

19. A radiotherapy unit according to claim 17, wherein a plurality of said leaf blocks is arranged in parallel, and
   said radiation part and said image sensors placed corresponding to predetermined leaf blocks and said radiation part, and said image sensors placed corresponding to the other leaf blocks adjacent to the predetermined leaf blocks, are differently arranged in line at the locations of placement.

20. A radiotherapy unit according to claim 17, wherein a plurality of said leaf blocks is arranged in parallel,
   a plurality of said radiation parts are placed corresponding to each leaf block in pairs, a plurality of said image sensors are placed corresponding to said radiation part in pairs,
   said radiation part irradiates a beam with a wavelength different from that of said radiation part corresponding to the other leaf blocks adjacent to corresponding leaf blocks, and
   said image sensors are provided with filters for transilluminating a beam with a wavelength irradiated by a pair of said radiation part.

21. A radiotherapy unit according to claim 17, wherein a plurality of said leaf blocks is arranged in parallel,
   a plurality of said radiation parts are placed corresponding to each leaf block in pairs,
   a plurality of said image sensors are placed corresponding to said radiation part in pairs,
   said radiation part irradiates a beam with a wavelength different from that of said radiation part corresponding to the other leaf blocks adjacent to corresponding leaf blocks, and
   said detection part further comprises an extraction part acquiring images obtained by irradiation of the radiation part by extracting only images created by a beam with a wavelength irradiated by said radiation part paired with the image sensors.

22. A radiotherapy unit comprising:
   a radiation source for irradiating radiation;
   a bed on which to place an object; and
   a multi-leaf collimator between said radiation source and said bed, narrowing a radiation field to a predetermined shape, said multi-leaf collimator comprising:
      leaf blocks movable in the direction of scaling the radiation field and having a pattern drawn along the direction of movement on a predetermined surface; and
      a detection part configured to acquire an image of the pattern included in a region along said predetermined surface and to detect displacement of said leaf blocks based on a temporal change of said images.

23. A radiotherapy unit according to claim 22, wherein said pattern has location-specific markings in parallel along a drawing area, and
   said detection part specifies the arranged locations of said pattern according to said location-specific markings.

24. A radiotherapy unit according to claim 22, wherein said detection part comprises:
   a radiation part irradiating a beam in the direction of said predetermined surface;
   image sensors subject to light reflected from the direction of said predetermined surface and acquiring said images; and
   a location acquisition part acquiring the locations of said leaf blocks from pattern images existing in said images.

25. A radiotherapy unit according to claim 24, wherein said location acquisition part comprises:

a recognition part recognizing the arranged locations of the pattern existing in said images, wherein, the locations of said leaf blocks are acquired according to locations of said arranged pattern.

26. A radiotherapy unit according to claim 24, wherein a plurality of said leaf blocks is arranged in parallel, and said radiation part and said image sensors placed corresponding to predetermined leaf blocks, and said radiation part and said image sensors placed corresponding to the other leaf blocks adjacent to the predetermined leaf blocks, are differently arranged in line at the locations of placement.

27. A radiotherapy unit according to claim 24, wherein a plurality of said leaf blocks is arranged in parallel, a plurality of said radiation parts are placed corresponding to each leaf block in pairs, a plurality of said image sensors are placed corresponding to said radiation part in pairs, said radiation part irradiates a beam with a wavelength different from that of said radiation part corresponding to the other leaf blocks adjacent to corresponding leaf blocks, and said image sensors are provided with filters for transilluminating a beam with a wavelength irradiated by a pair of said radiation part.

28. A radiotherapy unit according to claim 24, wherein a plurality of said leaf blocks is arranged in parallel, a plurality of said radiation parts are placed corresponding to each leaf block in pairs, a plurality of said image sensors are placed corresponding to said radiation part in pairs, said radiation part irradiates a beam with a wavelength different from that of said radiation part corresponding to the other leaf blocks adjacent to corresponding leaf blocks, and said detection part further comprises an extraction part acquiring images obtained by irradiation of the radiation part by extracting only images created by a beam with a wavelength irradiated by said radiation part paired with the image sensors.

* * * * *